United States Patent
Gilbert

(10) Patent No.: US 9,366,703 B2
(45) Date of Patent: *Jun. 14, 2016

(54) SYSTEM AND METHOD FOR VOLTAGE AND CURRENT SENSING

(71) Applicant: COVIDIEN LP, Mansfield, MA (US)

(72) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/808,981

(22) Filed: Jul. 24, 2015

(65) Prior Publication Data

US 2015/0331020 A1    Nov. 19, 2015

Related U.S. Application Data

(63) Continuation of application No. 14/069,610, filed on Nov. 1, 2013, now Pat. No. 9,116,179.

(60) Provisional application No. 61/738,045, filed on Dec. 17, 2012.

(51) Int. Cl.
| | |
|---|---|
| *G01R 15/18* | (2006.01) |
| *G01R 19/28* | (2006.01) |
| *G01R 1/20* | (2006.01) |
| *A61B 18/12* | (2006.01) |
| *A61B 18/14* | (2006.01) |
| *A61B 18/00* | (2006.01) |

(52) U.S. Cl.
CPC  *G01R 19/28* (2013.01); *G01R 1/20* (2013.01); *G01R 15/181* (2013.01); *A61B 18/1206* (2013.01); *A61B 18/1402* (2013.01); *A61B 18/1445* (2013.01); *A61B 2018/00827* (2013.01)

(58) Field of Classification Search
CPC .... G01R 15/181; G01R 15/183; G01R 15/18; G01R 15/186; G01R 33/07; G01R 33/09; G01R 33/02; H01F 3/10; H01F 3/14
USPC .............................. 324/127, 126, 117 R, 244
See application file for complete search history.

(56) References Cited

U.S. PATENT DOCUMENTS

| | | |
|---|---|---|
| 3,252,052 A | 5/1966 | Nash |
| 3,601,126 A | 8/1971 | Estes |
| 3,683,923 A | 8/1972 | Anderson |
| 3,697,808 A | 10/1972 | Lee |
| 3,885,569 A | 5/1975 | Judson |
| 3,913,583 A | 10/1975 | Bross |

(Continued)

FOREIGN PATENT DOCUMENTS

| | | |
|---|---|---|
| EP | 694291 A1 | 1/1996 |
| EP | 2281521 A1 | 2/2011 |

(Continued)

OTHER PUBLICATIONS

Extended European Search Report corresponding to European Application No. 13196200.3, dated Apr. 24, 2014; 6 pages.

(Continued)

*Primary Examiner* — Tung X Nguyen
*Assistant Examiner* — Thang Le

(57) ABSTRACT

A current sensor includes a Rogowski coil disposed on a flexible printed circuit board with at least one active lead passing through the Rogowski coil.

10 Claims, 19 Drawing Sheets

(56) References Cited

U.S. PATENT DOCUMENTS

| | | | |
|---|---|---|---|
| 4,102,341 A | | 7/1978 | Ikuno et al. |
| 4,378,525 A | * | 3/1983 | Burdick .................. G01R 1/22 |
| | | | 324/117 R |
| 4,437,464 A | | 3/1984 | Crow |
| 4,569,345 A | | 2/1986 | Manes |
| 4,621,231 A | * | 11/1986 | Heinrich ............. H01F 27/2804 |
| | | | 29/602.1 |
| 4,754,757 A | | 7/1988 | Feucht |
| 5,067,953 A | | 11/1991 | Feucht |
| 5,540,684 A | | 7/1996 | Hassler, Jr. |
| 5,817,091 A | | 10/1998 | Nardella et al. |
| 5,830,212 A | | 11/1998 | Cartmell et al. |
| 6,313,623 B1 | | 11/2001 | Kojovic et al. |
| 6,380,727 B1 | * | 4/2002 | Jitaru .................. G01R 15/148 |
| | | | 324/117 R |
| 6,440,157 B1 | | 8/2002 | Shigezawa et al. |
| 6,511,478 B1 | | 1/2003 | Burnside et al. |
| 6,624,624 B1 | * | 9/2003 | Karrer ................ G01R 15/181 |
| | | | 324/117 R |
| 6,731,193 B2 | | 5/2004 | Meier et al. |
| 6,822,547 B2 | | 11/2004 | Saito et al. |
| 6,979,329 B2 | | 12/2005 | Burnside et al. |
| 7,041,096 B2 | | 5/2006 | Malis et al. |
| 7,106,162 B2 | | 9/2006 | Saito |
| 7,158,012 B2 | * | 1/2007 | Wiesman ................ H04B 3/56 |
| | | | 324/126 |
| 7,736,359 B2 | | 6/2010 | McPherson |
| 8,152,800 B2 | | 4/2012 | Behnke |
| 8,198,885 B2 | * | 6/2012 | Sorensen ............. G01R 15/181 |
| | | | 324/117 H |
| 8,339,132 B2 | * | 12/2012 | Honkura ................ G01C 17/30 |
| | | | 324/244 |
| 8,398,627 B2 | | 3/2013 | Hosier |
| 9,116,179 B2 | | 8/2015 | Gilbert |
| 2003/0137388 A1 | * | 7/2003 | Meier .................. G01R 15/186 |
| | | | 336/225 |
| 2003/0181898 A1 | | 9/2003 | Bowers |
| 2004/0130318 A1 | * | 7/2004 | Saltsov .................. G01D 5/204 |
| | | | 324/207.17 |
| 2004/0178875 A1 | | 9/2004 | Saito |
| 2004/0257061 A1 | | 12/2004 | George de Buda |
| 2007/0063664 A1 | | 3/2007 | Rhodes et al. |
| 2008/0071260 A1 | | 3/2008 | Shores |
| 2008/0079418 A1 | * | 4/2008 | Rea ..................... G01R 15/181 |
| | | | 324/117 R |
| 2009/0013526 A1 | | 1/2009 | Yang et al. |
| 2009/0036883 A1 | | 2/2009 | Behnke |
| 2009/0066317 A1 | * | 3/2009 | de Buda ................ H04B 3/56 |
| | | | 324/103 R |
| 2009/0243590 A1 | * | 10/2009 | West ..................... G01R 19/04 |
| | | | 324/117 R |
| 2010/0114090 A1 | | 5/2010 | Hosier |
| 2013/0023870 A1 | | 1/2013 | Collins |
| 2013/0023871 A1 | | 1/2013 | Collins |
| 2014/0210463 A1 | * | 7/2014 | Klein ................ G01R 33/0052 |
| | | | 324/253 |

FOREIGN PATENT DOCUMENTS

| | | |
|---|---|---|
| EP | 2407116 A1 | 1/2012 |
| EP | 2510895 A1 | 10/2012 |
| WO | 0072027 A1 | 11/2000 |
| WO | 02/00129 | 1/2002 |
| WO | 2010007017 A1 | 1/2010 |

OTHER PUBLICATIONS

Extended European Search Report corresponding to European Application No. 13196199.7, dated Apr. 25, 2014; 6 pages.

* cited by examiner

SYSTEM AND METHOD FOR VOLTAGE AND CURRENT SENSING

CROSS REFERENCE TO RELATED APPLICATIONS

The present application is a continuation application of U.S. patent application Ser. No. 14/069,610, filed on Nov. 1, 2013, which claims the benefit of and priority to U.S. Provisional Application Ser. No. 61/738,045, filed on Dec. 17, 2012, the entire contents of each of which are incorporated herein by reference.

BACKGROUND

1. Technical Field

The present disclosure relates to an electrosurgical system and method for operating an electrosurgical generator. More particularly, the present disclosure relates to a system and method for measuring output radio frequency (RF) voltage and current in an electrosurgical generator.

2. Background of Related Art

Electrosurgery involves application of high radio frequency (RF) electrical energy to a surgical site to cut, ablate, or coagulate tissue. During treatment, the surgeon selects the desired tissue effect by setting controls on an electrosurgical generator and brings an electrosurgical instrument (e.g., monopolar, bipolar, etc.) into contact with the surgical site such that the instrument applies electrosurgical energy to the tissue.

Electrosurgical energy outputted by the generator has a predetermined voltage and current. The generator may also be configured to modify properties of the voltage and current waveforms, such as amplitude, phase, and duration to achieve as desired tissue effect, such as, cutting, ablation, coagulation, vessel sealing, and combinations thereof.

The generator may also include voltage and current sensors for monitoring the voltage and current at the surgical site. The generator utilizes the sensor readings to adjust the energy delivered to the surgical site so that it matches the settings inputted by the surgeon.

Existing electrosurgical generators include transformers having a high permeability material (e.g., ferrite) to sense the voltage and current of the electrosurgical energy and isolate the patient. High permeability materials are limited for surgical use since the output of the transformers is non-linear, fluctuates with temperature, and the overall tolerances of the transformers are not well-controlled. These limitations cause the sensed signals to be less accurate than desired.

SUMMARY

The present disclosure provides a current sensor including: a Rogowski coil disposed on a flexible printed circuit board with at least one active lead passing through the Rogowski coil.

According to another aspect of the above embodiment, the Rogowski coil includes: an outer coil having an upper portion and a lower portion interconnected by a plurality of vias; and an inner conductor disposed within the outer coil.

According to another aspect of the above embodiment, the flexible printed circuit board includes: a first layer including the upper portion of the outer coil; a second layer including the inner conductor; and a third layer including the lower portion of the outer coil.

According to another aspect of the above embodiment, the first layer is coupled to the second layer and is pivotable relative thereto.

The current sensor according to claim 3, wherein the second layer is coupled to the third layer and is pivotable relative thereto.

According to another aspect of the above embodiment, the first, second, and third layers are folded over each other to enclose the inner conductor between the upper and lower portions of the outer coil.

According to another aspect of the above embodiment, the outer coil and the inner conductor are coupled to a conditioning circuit and output a differentiated signal corresponding to a current passing through at least one active lead to the conditioning circuit.

According to another aspect of the above embodiment, the conditioning circuit is configured to integrate the differentiated signal to output a processed current signal indicative of the current.

The present disclosure provides a current sensor including: a Rogowski coil disposed on a flexible printed circuit board with at least one active lead passing through the Rogowski coil, the Rogowski coil configured to output a differentiated signal corresponding to a current passing through at least one active lead; and a conditioning circuit coupled to the Rogowski coil, the conditioning circuit configured to integrate the differentiated signal to output a processed current signal indicative of the current.

According to another aspect of the above embodiment, the conditioning circuit includes a first portion and a second portion interconnected by the flexible printed circuit board.

According to another aspect of the above embodiment, the at least one active lead is disposed between the first and second portions of the conditioning circuit.

According to another aspect of the above embodiment, the Rogowski coil includes: an outer coil having an upper portion and a lower portion interconnected by a plurality of vias; and an inner conductor disposed within the outer coil.

According to another aspect of the above embodiment, the flexible printed circuit board includes: a first layer including the upper portion of the outer coil; a second layer including the inner conductor; and a third layer including the lower portion of the outer coil.

According to another aspect of the above embodiment, the first layer is coupled to the second layer and is pivotable relative thereto According to another aspect of the above embodiment, the second layer is coupled to the third layer and is pivotable relative thereto.

According to another aspect of the above embodiment, wherein the first, second, and third layers are folded over each other to enclose the inner conductor between the upper and lower portions of the outer coil.

The present disclosure provides a current sensor including: a Rogowski coil disposed on a flexible printed circuit board with at least one active lead passing through the Rogowski coil, the Rogowski coil configured to output a differentiated signal corresponding to a current passing through at least one active lead, wherein the Rogowski coil includes: an outer coil having an upper portion and a lower portion interconnected by a plurality of vias; and an inner conductor disposed within the outer coil; and a conditioning circuit coupled to the Rogowski coil, the conditioning circuit configured to integrate the differentiated signal to output a processed current signal indicative of the current.

According to another aspect of the above embodiment, the conditioning circuit includes a first portion and a second portion interconnected by the flexible printed circuit board and the at least one active lead is disposed between the first and second portions of the conditioning circuit.

According to another aspect of the above embodiment, the flexible printed circuit board includes: a first layer including the upper portion of the outer coil; a second layer including the inner conductor; and a third layer including the lower portion of the outer coil.

According to another aspect of the above embodiment, the first, second, and third layers are folded over each other to enclose the inner conductor between the upper and lower portions of the outer coil as first and second portions are approximated relative to each other.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides a current sensor configured to measure an AC current of a first conductor. The current sensor includes an outer coil with a first portion and a second portion. Each of the first and second portions form half of a toroid about the first conductor and the first conductor is disposed through a center of the outer coil. The current sensor includes an inner conductor disposed within the first and second portions of the outer coil, and a conditioning circuit. The conditioning circuit includes a first connector coupled to the first portion of the outer coil and a second connector coupled to the second portion of the outer coil, and the conditioning circuit is configured to amplify and integrate a voltage received from the first and second connections and to output a measured AC current of the first conductor.

A generator according to the present disclosure can perform monopolar and/or bipolar electrosurgical procedures, including vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cutting, blending, division, etc.) and procedures (e.g., monopolar, bipolar, vessel sealing). In embodiments, the generator may be embedded, integrated or otherwise coupled to the electrosurgical instruments providing for an all-in-one electrosurgical apparatus.

Figure 1:
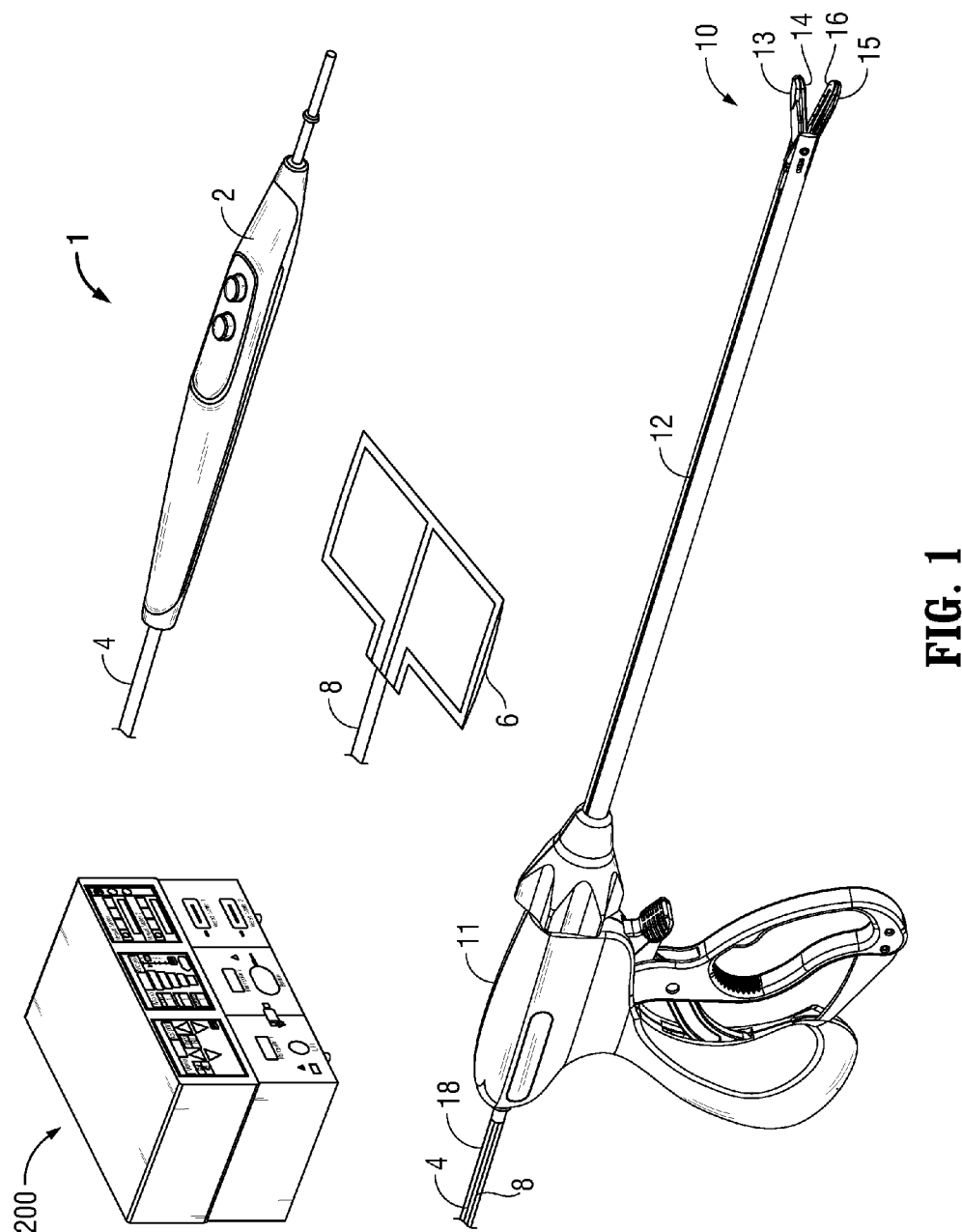
FIG. 1 is a schematic block diagram of an embodiment of an electrosurgical system according to the present disclosure.

FIG. 1 is a schematic illustration of a bipolar and monopolar electrosurgical system 1 according to the present disclosure. The system 1 may include one or more monopolar electrosurgical instruments 2 having one or more electrodes (e.g., electrosurgical cutting probe, ablation electrode(s), etc.) for treating tissue of a patient. Electrosurgical energy is supplied to the instrument 2 by a generator 200 via a supply line 4 that is connected to an active terminal 230 (FIG. 3) of the generator 200, allowing the instrument 2 to coagulate, ablate and/or otherwise treat tissue. The energy is returned to the generator 200 through a return electrode 6 via a return line 8 at a return terminal 232 (FIG. 3) of the generator 200. The system 1 may include a plurality of return electrodes 6 that are disposed on a patient to minimize the chances of tissue damage by maximizing the overall contact area with the patient. In addition, the generator 200 and the return electrode 6 may be configured for monitoring so-called "tissue-to-patient" contact to insure that sufficient contact exists therebetween to further minimize chances of tissue damage.

Figure 3:
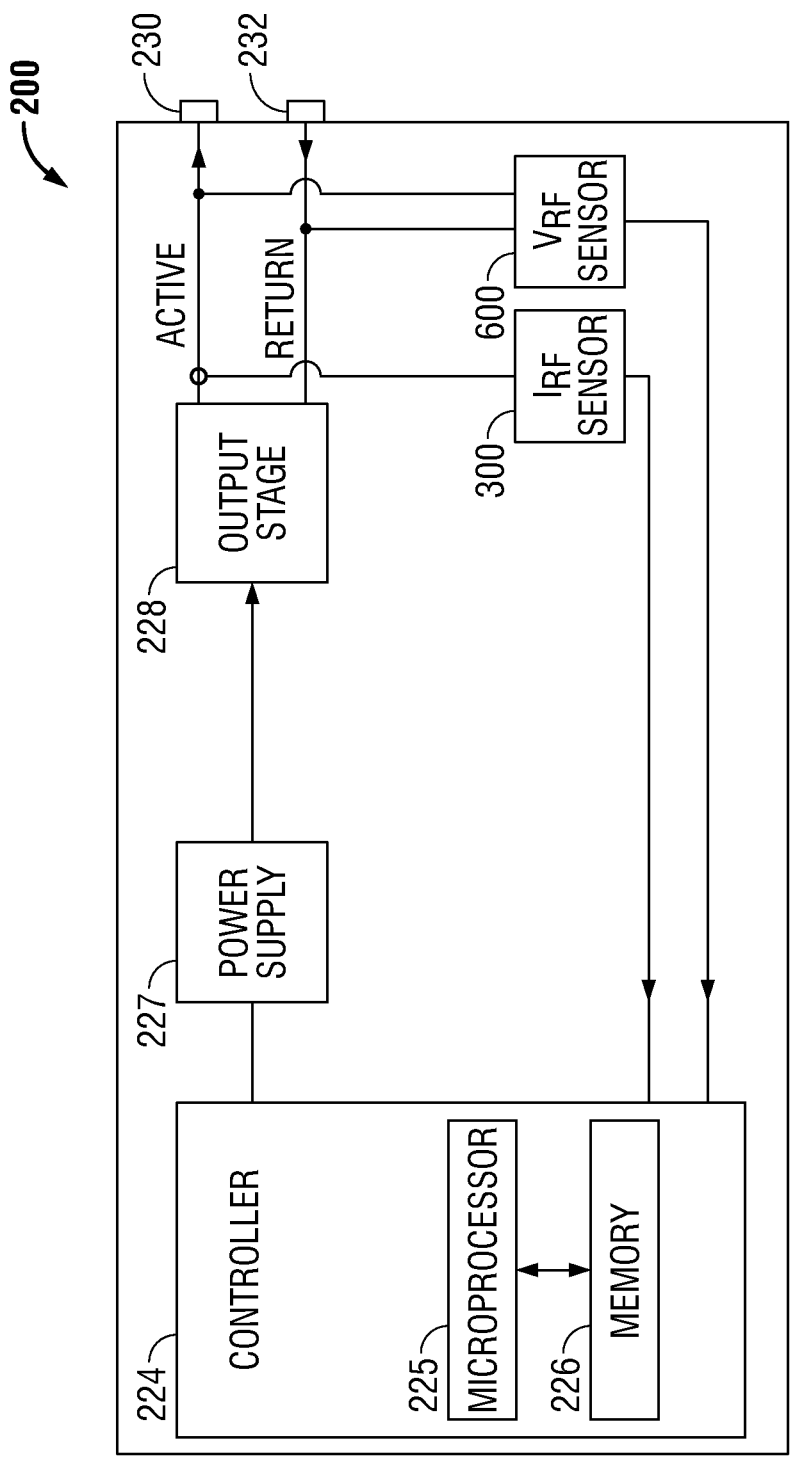
FIG. 3 is a schematic block diagram of the electrosurgical generator of FIG. 2 according to the present disclosure.

The system 1 may also include a bipolar electrosurgical forceps 10 having one or more electrodes for treating tissue of a patient. The electrosurgical forceps 10 includes a housing 11 and opposing jaw members 13 and 15 disposed at a distal end of a shaft 12. The jaw members 13 and 15 have one or more active electrodes 14 and a return electrode 16 disposed therein, respectively. The active electrode 14 and the return electrode 16 are connected to the generator 200 through cable 18 that includes the supply and return lines 4, 8 coupled to the active and return terminals 230, 232, respectively (FIG. 3). The electrosurgical forceps 10 is coupled to the generator 200 at a connector having connections to the active and return terminals 230 and 232 (e.g., pins) via a plug disposed at the end of the cable 18, wherein the plug includes contacts from the supply and return lines 4, 8 as discussed in more detail below.

Figure 2:
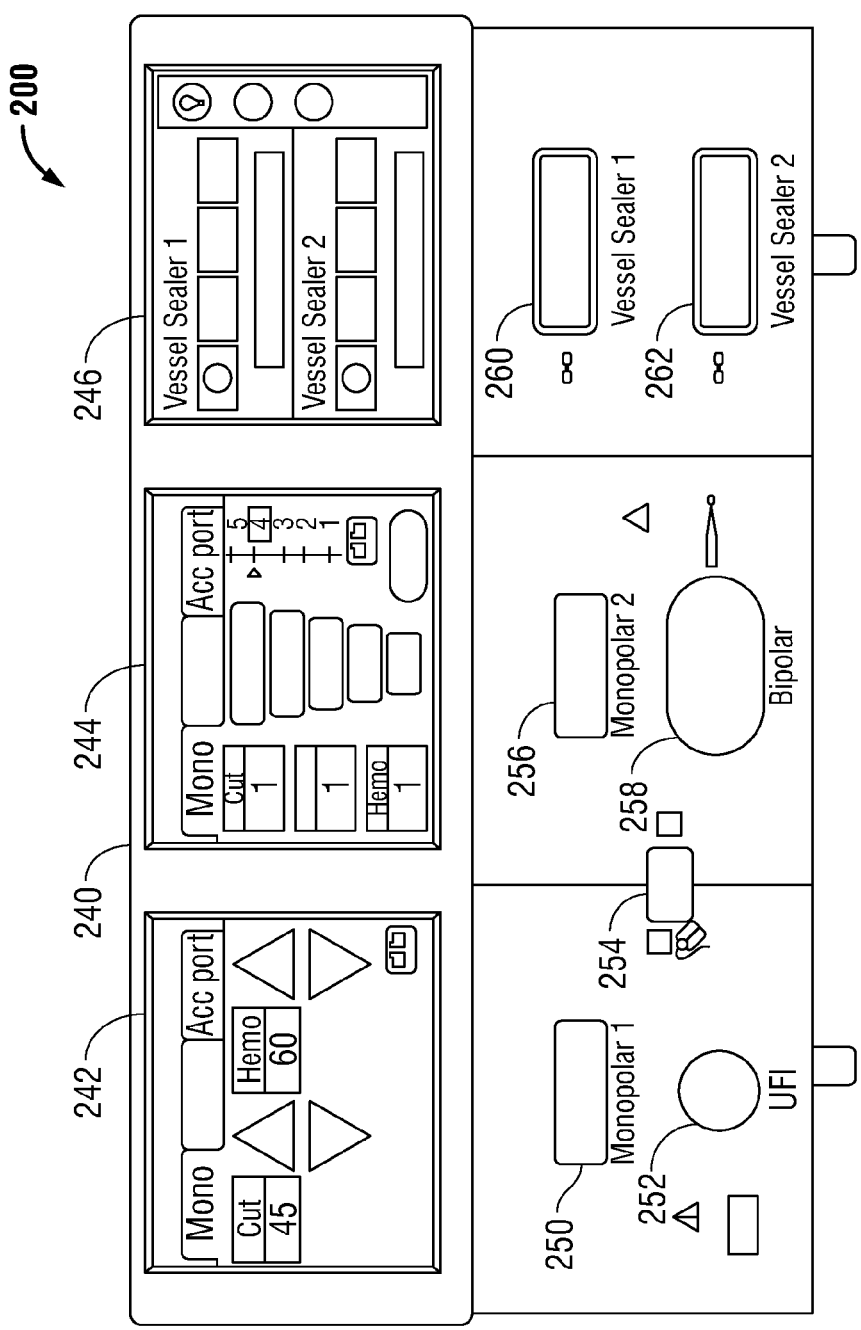
FIG. 2 is a front view of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 10, etc.). The connectors 250-262 may include various detection devices that can read (e.g., scan, decode, etc.) identifying information encoded or otherwise recorded on or within the plugs or cables of the instruments. The connectors 250-262 are configured to decode the information encoded on the plugs corresponding to the operating parameters of particular instruments allowing the generator 200 to preset energy delivery settings based on the connected instrument. In embodiments, data may be encoded in bar codes, electrical components (e.g., resistors, capacitors, etc.), RFID chips, magnets, non-transitory storage (e.g., non-volatile memory, EEPROM, etc.), which may then be coupled to or integrated into the plug. Corresponding detection devices may include, but are not limited to, bar code readers, electrical sensors, RFID readers, Hall Effect sensors, memory readers, etc. and any other suitable decoders configured to decode data.

The generator 200 includes one or more display screens 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 10, etc.). The user then makes inputs by simply touching corresponding menu options.

Screen 242 controls monopolar output and the devices connected to the connectors 250 and 252. Connector 250 is configured to couple to monopolar electrosurgical instrument (e.g., electrosurgical pencil) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 10 that may be plugged into the connectors 260 and 262. The generator 200 outputs energy through the connectors 260 and 262 suitable for sealing tissue grasped by the forceps 10. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as pressure, sealing duration, etc. The user-defined setting is transmitted to the controller 224 where the setting may be saved in memory 226. In embodiments, the intensity setting may be a number scale, such as from one to ten or one to five. In embodiments, the intensity setting may be associated with an output curve of the generator 200. The intensity settings may be specific for each forceps 10 being utilized, such that various instruments provide the user with a specific intensity scale corresponding to the forceps 10.

FIG. 3 shows a schematic block diagram of the generator 200 configured to output electrosurgical energy. The generator 200 includes a controller 224, a power supply 227, and an output stage 228. The power supply 227 may be a direct current high voltage power supply and that connects to an AC source (e.g., line voltage) and provides high voltage DC power to an output stage 228, which then converts high voltage DC power into treatment energy (e.g., ultrasonic, electrosurgical or microwave) and delivers the energy to the active terminal 230. The energy is returned thereto via the return terminal 232. The output stage 228 is configured to operate in a plurality of modes, during which the generator 200 outputs corresponding waveforms having specific duty cycles, peak voltages, crest factors, etc. In another embodiment, the generator 200 may be based on other types of suitable power supply topologies.

The controller 224 includes a microprocessor 225 operably connected to a memory 226, which may include transitory type memory (e.g., RAM) and/or non-transitory type memory (e.g., flash media, disk media, etc.). The microprocessor 225 includes an output port that is operably connected to the power supply 227 and/or output stage 228 allowing the microprocessor 225 to control the output of the generator 200 according to either open and/or closed control loop schemes. Those skilled in the art will appreciate that the microprocessor 225 may be substituted by any logic processor (e.g., control circuit) adapted to perform the calculations and/or set of instructions discussed herein.

A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or output stage 228, which then adjusts the DC and/or power supply, respectively. The controller 224 also receives input signals from the input controls of the generator 200, the instrument 2 and/or forceps 10, as described above. The controller 224 utilizes the input signals to adjust power outputted by the generator 200 in the closed control loop and/or performs other control functions thereon.

The generator 200 according to the present disclosure includes an RF current sensor 300 and an RF voltage sensor 600. The RF current sensor 300 is coupled to the active terminal 230 and provides measurements of the RF current supplied by the output stage 228. The RF voltage sensor 600 is coupled to the active and return terminals 230 and 232 provides measurements of the RF voltage supplied by the output stage 228. In embodiments, the RF current and voltage sensors 300 and 600 may be coupled to active and return leads 228a and 228b, which interconnect the active and return terminals 230 and 232 to the output stage 228, respectively. The RF current and voltage sensors 300 and 600 provide the sensed RF voltage and current signals, respectively, to the controller 224, which then may adjust output of the power supply 227 and/or the output stage 228 in response to the sensed RF voltage and current signals. Various components of the generator 200, namely, the output stage 228, the RF current and voltage sensors 300 and 600, may be disposed on a printed circuit board (PCB).

Transformers are conventionally used as current and voltage sensors as they provide a required patient isolation. However, transformers provide fluctuating readings due to temperature, signal amplitude, etc. This makes accurate readings difficult with respect to phase and gain-bandwidth of the sensor signals. As a result, the signals need to be post-processed to arrive at accurate signals. The present disclosure provides for novel RF voltage and current sensors 300 and 600 which overcome the problems of conventional sensors.

Figure 4:
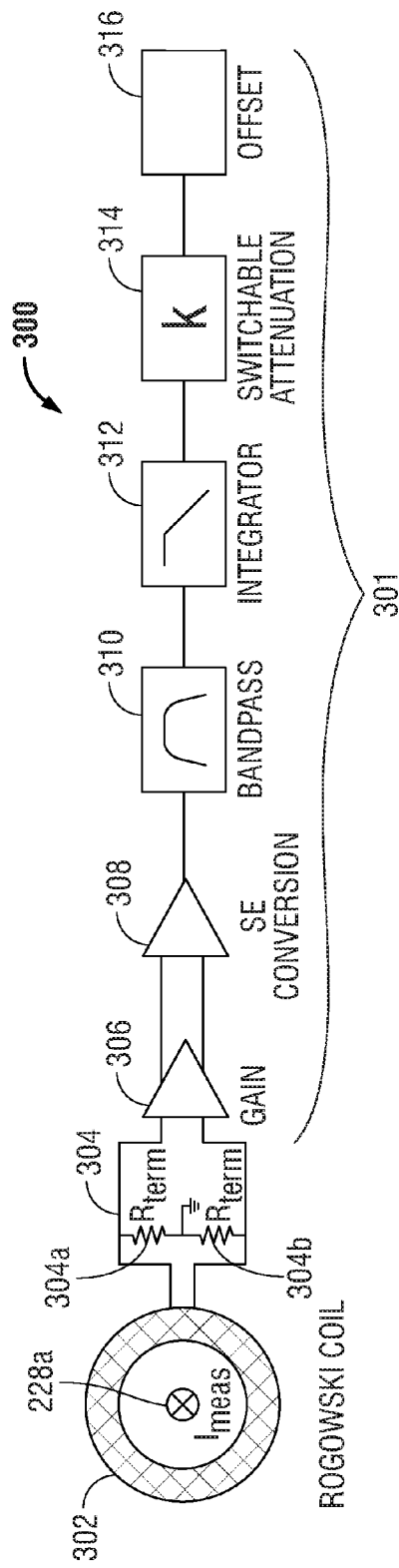
FIG. 4 is a schematic diagram of a current sensor according to the present disclosure.

FIG. 4 shows the RF current sensor 300 which includes a Rogowski coil 302. As used herein, the term "Rogowski coil" refers to an electrical device for measuring alternating current (e.g., RF current) and includes an outer conductor coil (e.g., toroid) that acts as an active conductor wrapped around an inner conductor, a so-called "Bucking coil" that acts as a return conductor with a lead carrying the current passing through the center of the coil. The coil may have any suitable shape such as helical, toroidal, etc. In embodiments, the coil may have a polygonal cross-section. The Rogowski coil may include a low permeability core (e.g., air core) that provides a voltage output having a time-derivate of the current being measured to a conditioning circuit that integrates the output to provide a voltage signal indicative of the current. In embodiments, the Rogowski coil 302 may be implemented on a printed circuit board and may include a gap so that the Rogowski coil 302 may be wrapped about the conductor carrying the current to be measured.

As described in greater detail below, the Rogowski coil 302 of the present disclosure increases common mode voltage rejection due to the connection of the Bucking coil. Further, the conditioning circuit 301 according to the present disclosure is configured as a differential amplifier that improves the common-mode rejection ratio (CMRR) unlike prior art conditioning circuits which are usually single ended and thus, fail to increase CMRR.

The Rogowski coil 302 is coupled to a conditioning circuit 301 having a resistor divider 304, which includes resistors 304a and 304b. In embodiments, the conditioning circuit 301 may be implemented as any integrator (e.g., logic processor) or differential amplifier. The resistor divider 304 removes resonance of the coil 302 at the coil's resonant frequency. As described in further details below with respect to FIGS. 5-9, the Rogowski coil 302 is disposed about the active lead 228a, the coil 302 is configured to measure the current passing therethrough as a voltage signal. The voltage signal from the coil 302 is then supplied to an optional gain amplifier 306 which increases the amplitude of the voltage signal. The gain amplifier 306 or the coil 302, if the gain amplifier 306 is not used, is also coupled to a single-ended amplifier 308, which is, in turn, coupled to a bandpass filter 310. The single ended amplifier 308 is a differential-to-single-ended converter whose function is to convert the differential signal from the coil 302 to a single-ended signal. The amplifier 308 may have a monolithic configuration that provides improved common mode rejection.

The bandpass filter 310 removes higher and lower frequency components of the voltage signal which is then transmitted to an integrator 312. Since the voltage that is induced in the Rogowski coil 302 is proportional to the rate of change of current that is flowing through the active leads 228a the integrator 312 is utilized to provide an output voltage signal that is proportional to the current.

In embodiments, the integrator 312 may be coupled to switchable attenuation circuit 314, which may include one or more actively switched components. The attenuation circuit 314 may then be coupled to additional components such as an offset circuit 316, analog-digital converters, and the like prior to supplying the signal to the controller 224.

Figure 5:
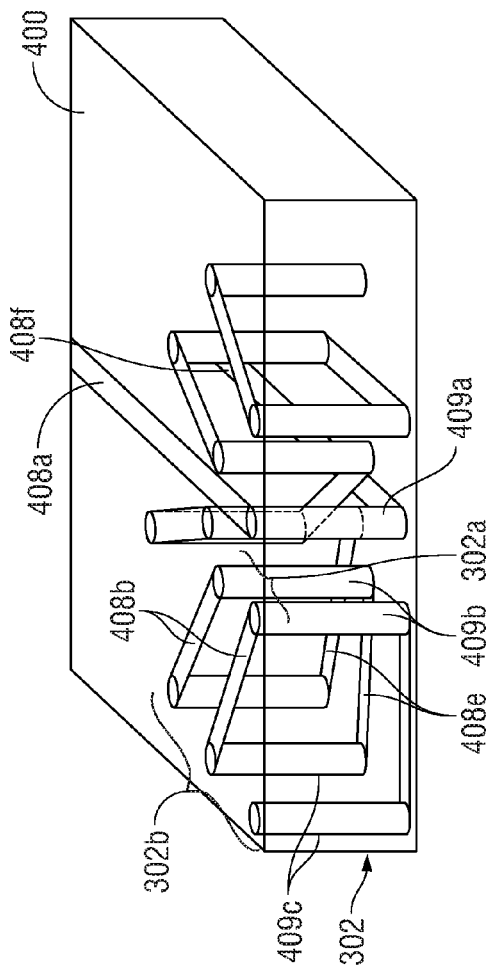
FIG. 5 is a partially-exposed, isometric view of a Rogowski coil disposed on a printed circuit board according to the present disclosure.
Figure 6:
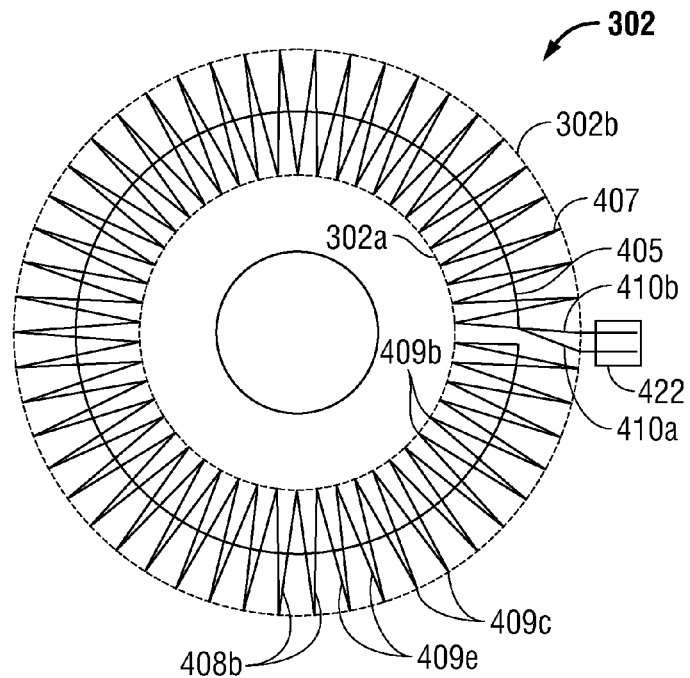
FIG. 6 is a partially-exposed, plan view of the Rogowski coil of FIG. 5 according to the present disclosure.

FIGS. 5-9 show the Rogowski coil 302 according to the present disclosure. The coil 302 has substantially a circular shape having an opening therethrough defined by inner circumferential region 302a (FIG. 6). The lead 228a is disposed through the opening 301 allowing the coil 302 to measure the current flow through the lead 228a.

As shown in FIGS. 5 and 6, the coil 302 has a substantially toroidal shape and is formed on a printed circuit board (PCB) 400 and includes and inner circumferential region 302a and an outer circumferential region 302b (FIG. 6). The coil 302 includes forming an inner portion ("Bucking coil") 405 of the coil 302 and an outer coil 407. In embodiments, the coil 302 may have any other suitable shape (e.g., having a polygonal cross-section) with the outer coil 407 wrapped about the inner portion 405 and defining an opening therethrough. In embodiments, the coil 302 may be a coil-wrapped phenolic toroid having a low permeability ($\mu_0$).

The current i(t) flowing through lead 228a produces a first magnetic field proportional to the rate of change of the sensed current i(t). The outer coil 407 detects the first magnetic field and produces a first voltage corresponding to the first magnetic field (e.g., field 1905 of FIGS. 19A-B). The outer coil 407 also detects a second magnetic field and produces a second voltage corresponding to the second magnetic field (e.g., field 1930 of FIGS. 19A-B). The second magnetic field is orthogonal to the first magnetic field and is not related to the sensed current. The inner portion 405 senses the second magnetic field and produces a third voltage proportional to the second magnetic field. The second voltage and third voltage produced have approximately the same magnitude and are connected so that they cancel each other out and are further removed through conditioning circuit 301.

Figure 8:
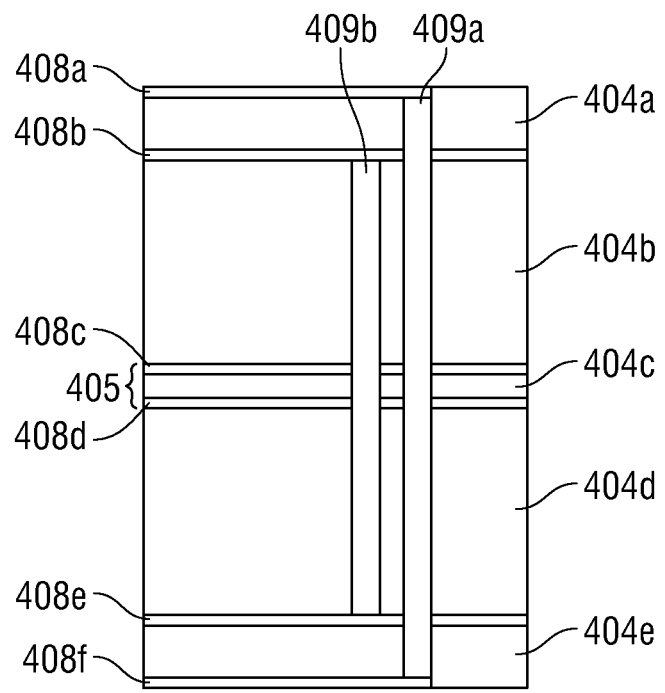
FIG. 8 is a side, cross-sectional view of the printed circuit board of FIG. 5 according to the present disclosure.
Figure 9:
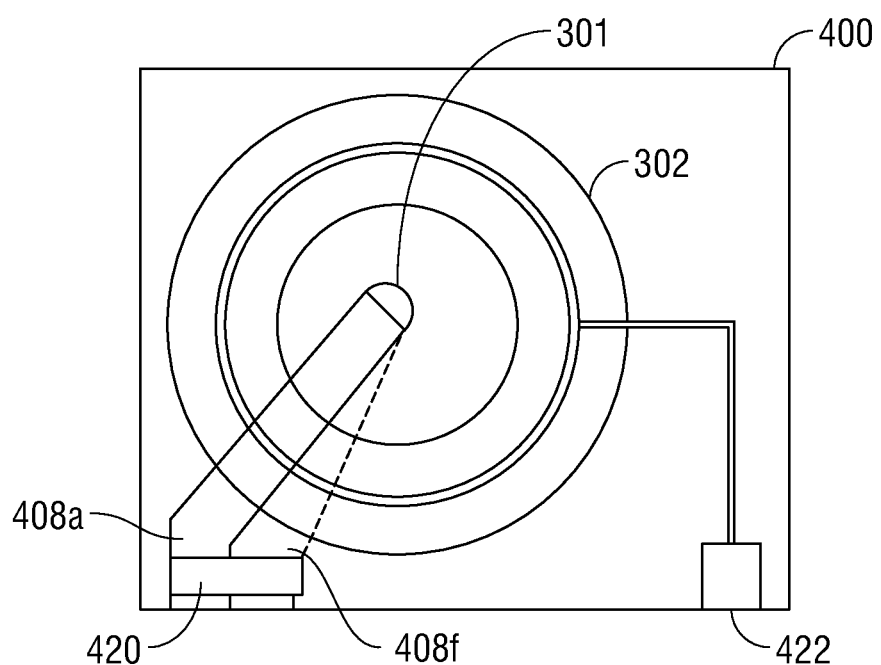
FIG. 9 is a plan view of the printed circuit board of FIG. 5 according to the present disclosure.

The PCB 400 may be a multilayer PCB formed from any suitable dielectric material, including, but not limited to, composite materials composed of woven fiberglass cloth with an epoxy resin binder such as FR-4. As shown in FIG. 8, the PCB 400 includes a first or top layer 404a and a bottom layer 404e of sufficient thickness to prevent capacitive coupling between conductive traces 408b and 408e. The active lead 228a is coupled to conductive traces 408a and 408f, respectively, which are disposed over the top and bottom layers 404a and 404e as shown in FIGS. 8 and 9. The active leads 228a may be coupled to a patient side connector 420 disposed on the PCB 400 as shown in FIG. 9. The traces 408a and 408f are interconnected through the center 301 via one or more vias 409a, which pass through the entire PCB 400 (e.g., layers 404a-404e).

The outer coil 407 includes a top trace 408b disposed between the top layer 404a and an intermediate layer 404b of the PCB 400. The outer coil 407 also includes a bottom trace 408e disposed between the bottom layer 404e and an intermediate layer 404d of the PCB 400. The traces 408b and 408e are interconnected by a plurality of inner vias 409b and outer vias 409c. The layers 404a and 404e insulate the coil 302 (e.g., outer coil 407), conductive traces 408a and 408f and provide an isolation barrier between the patient and the generator 200.

Figure 7:
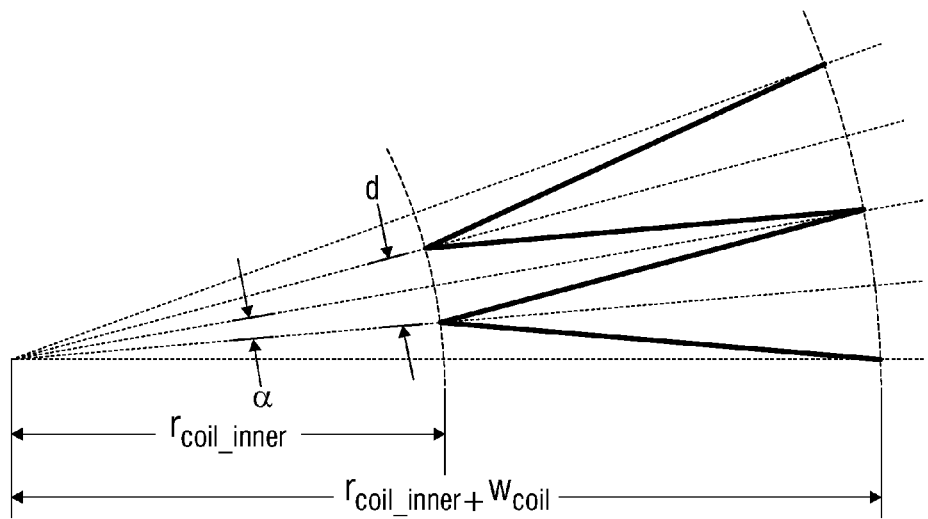
FIG. 7 is an enlarged schematic view of the Rogowski coil of FIG. 5 according to the present disclosure.
Figure 10A:
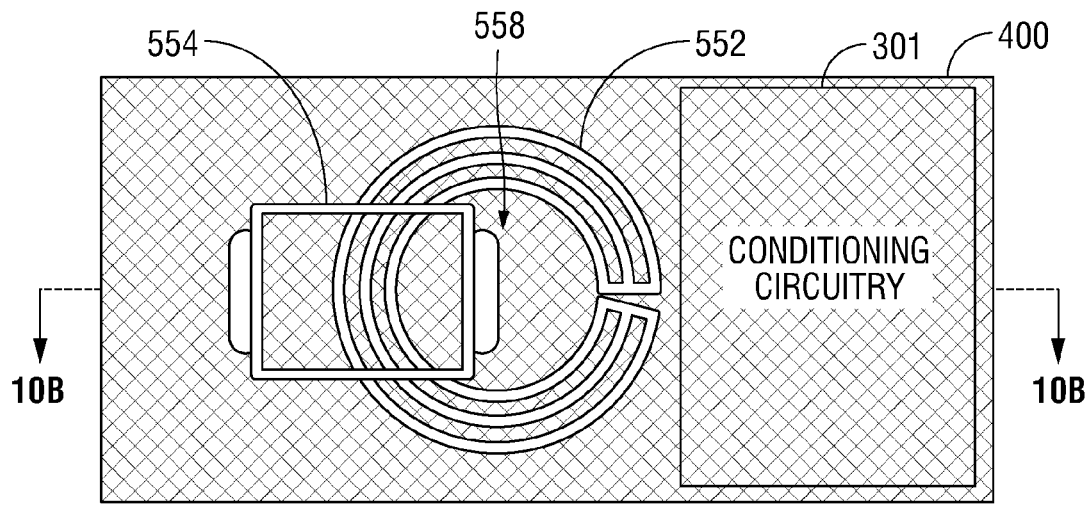
FIG. 10A is a plan view of a Rogowski coil disposed on a printed circuit board according to the present disclosure.
Figure 10B:
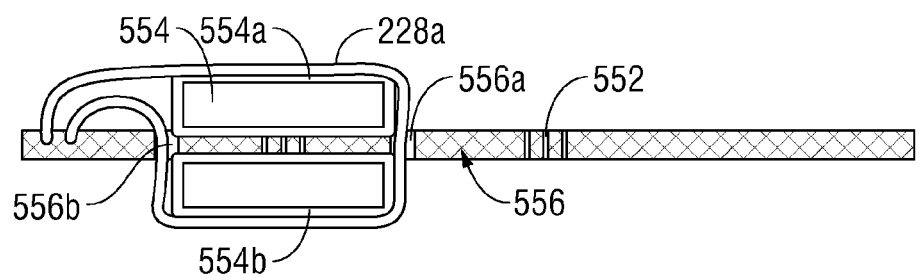
FIG. 10B is a side, cross-sectional view taken along 10B-10B of the Rogowski coil disposed on the printed circuit board according to the present disclosure.

As shown in FIGS. 5-7, the inner vias 409b are arranged to form the inner circumferential region 302a of the coil 302 and the outer vias 409c form the outer circumferential region 302b of the coil 302. The inner and outer vias 409b and 409c pass through the layers 404b, 404c, and 404d. The inner vias 409b and outer vias 409c may be disposed in a concentric configuration as shown in FIGS. 10A and 10B, respectively. In a concentric configuration, corresponding inner and outer vias 409b and 409c lie along the same rays. In a staggered configuration, the inner and outer vias 409b and 409c lie along alternating rays "r" as shown in FIGS. 5-7. The rays "r" are disposed at and an angle "α" relative to each other and the inner vias 409b are separated by a distance "d." Each of the inner vias 409b is connected to two neighboring outer vias 409c through traces 408a and 408e and vice versa. The interconnection of the vias 409b and 409c with the traces 408a and 408e forms a plurality of loops, which in turn, form the outer coil 407 as shown in FIG. 5.

The outer coil 407 may include any suitable number of turns, in embodiments from about 50 turns to about 100 turns. The maximum number of turns depends on the radius of the inner circumferential region 302a, via aspect ratio, thickness of the outer coil 407 and/or PCB 400, and spacing between the turns based on the limits of manufacturability of the PCB material (e.g., trace to trace, trace to via, via annular pad dimension, anything that may limit the placement of the conductors on the PCB).

With reference to FIGS. 6 and 8, the inner portion 405 is disposed within the outer coil 407 and also has a substantially circular shape. The inner portion 405 may include an upper trace 408c and a bottom trace 408d. The traces 408c and 408d are disposed over a dielectric layer 404c, such that the traces 408c and 408d are insulated from each other. The traces 408c and 408d may be electrically coupled to each other. In embodiments, the inner portion 405 may be formed from a single trace.

As shown in FIGS. 6 and 9, the coil 302 is coupled to the other components of the sensor 300 at a side connector 422, which may also disposed on the PCB 400. The coil 302 includes a first terminal 410a coupled to the inner portion 405 and a second terminal 410b coupled to the outer coil 407. In particular, the outer coil 407 is disposed over the inner portion 405 and is coupled thereto. Thus, two terminals 410a and 410b are disposed at one end of the coil 302. The interconnection between the inner portion 405 and the outer portion 407 as well as the connection to the terminals 410a and 410b may be made through the vias 409b and 409c.

The controller 224 is provided voltage signals from the sensor 300, which are then utilized to determine the current. Various formulas may be utilized by the controller 224 to determine the current. The voltage produced by the coil 302 may be calculated using the formula (I):

$$V_{OUT} = \frac{-A_{LOOP} N_{LOOPS}}{2\pi R_{COIL}} \mu_0 \frac{dI}{dt} \quad (I)$$

In formula (I), A is the area of the turn (e.g., loop) formed by the vias 409b and 409c with the traces 408a and 408b, N is the number of turns, R is the major radius of the coil 302, $\mu_0$ to is the magnetic constant, dI/dt is the rate of change of the current being measured by the coil 302.

Inductance and capacitance of the coil may be calculated using the formulae (II)-(IV), respectively. Capacitance of the coil 302 is used to determine self-resonance and may be calculated using parallel-wire model formulae, namely, capacitances of inner and outer vias 409b and 409c and traces 408a and 408b.

$$L_{Coil} = \frac{\mu_0 \cdot N_{Turns}^2 \cdot l_{coil}}{2\pi} \ln\left(\frac{r_{coil\_inner} + w_{coil}}{r_{coil\_inner}}\right) \quad (II)$$

$$C_{Coil} = N_{Turns} \cdot (2 \cdot C_{trace-trace} + C_{via-inner} + C_{via-outer}) \quad (III)$$

$$C_{\parallel} = \frac{\pi \cdot \varepsilon_0 \cdot \varepsilon_r \cdot l_{trace/via}}{\ln\left(\frac{d_{between\_trace/via}}{2 \cdot r_{via/trace}} + \sqrt{\frac{d_{between\_trace/via}^2}{r_{via/trace}^2} - 1}\right)} \quad (IV)$$

In formulae (II)-(IV), in addition to the variable and constants utilized in formula (I), t is thickness (e.g., distance between conductive traces 408b and 408e), r is radius, w is the radial distance between inner and outer circumferential regions 302a and 302b, Rcoil_inner is the radial distance to the inner circumferential region 302a, l is length, $\varepsilon_0$ is vacuum permittivity constant, and $\varepsilon_r$ is the dielectric constant of the PCB.

FIGS. 10A and 10B show another embodiment of a Rogowski coil 552. The coil 552 is substantially similar to the coil 302. The coil 552 is also coupled to the conditioning circuit 301, which is disposed on the PCB 400. In this embodiment, the coil 552 is formed within the PCB 400 and the lead 228a may pass directly through the coil 552. The PCB 400 includes one or more openings 556a and 556b, with the opening 556a passing through an opening 558 defined within the coil 552. The leads 228a may be wound about a spacer 554, which is disposed between the openings 556a and 556b, which aligns the leads 228a for passage through the coil 552. The coil 552 operates in the same manner as described above with respect to the coil 302 by sensing the current passing through the leads 228a. The leads 228a may be wrapped around a spacer 554 disposed between the openings 556a and 556b, which aligns the leads 228a for passage through the coil 552. The spacer 554 may include an upper portion 554a and a lower portion 554b disposed on each side of the PCB 400.

With reference to FIGS. 4 and 11-15, conditioning circuit 301 of the sensor 300 is shown. Since the coil 302 provides a differentiating response, the output must be integrated to provide the actual response via the conditioning circuit 301 of the sensor 300. The output of the coil 302 is integrated to produce a signal that is proportional to the current in the active lead 228a. The conditioning circuit 301 provides integration via the integrator 312. This allows for easy adjustability of the sensor gain. Gain may be set by adjusting the frequency setpoint of the integrator 312. The setpoint may be achieved by the selection of hardware component values (e.g., discrete resistor or capacitor substitution), the selection of software values (e.g., digital or analog potentiometers or adjustable capacitors), including programmable gain amplifiers as described in detail below, or combinations thereof.

Figure 11:
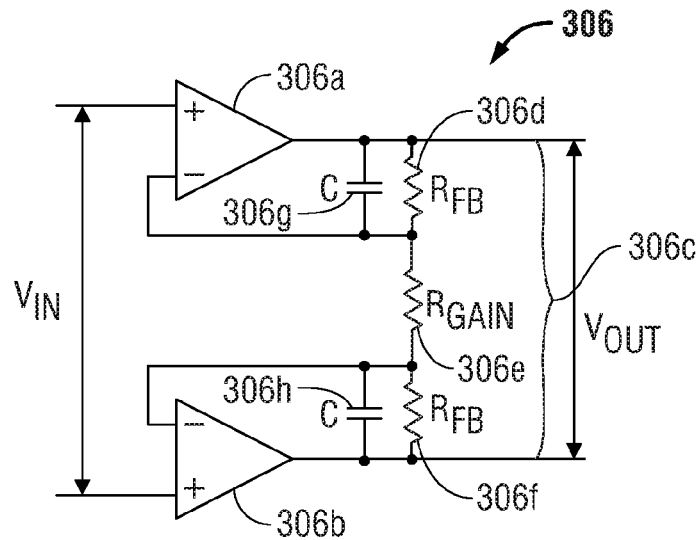
FIG. 11 is a schematic circuit diagram of a gain amplifier according to the present disclosure.

The gain amplifier 306 of the conditioning circuit 301 is shown in FIG. 11 and includes a pair of operation amplifiers 306a and 306b configured to provide differential gain without adding to the common-mode gain. The voltage signal from the coil 302 is provided to the positive terminals of the amplifiers 306a and 306b. The outputs of the amplifiers 306a are interconnected by a voltage divider network 306c including three resistors 306d, 306e, 306f. Terminal resistors 306d and 306f are coupled in parallel with capacitors 306g and 306h, respectively. The signal from the parallel circuits is coupled to the negative terminals of the amplifiers 306a and 306b, which provide closed-loop feedback thereto. These capacitors 306g and 306h provide amplifier stabilization and may also provide for the integration of the signal.

Figure 12:
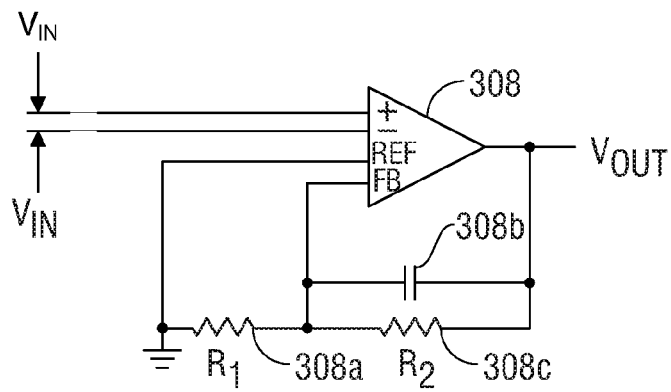
FIG. 12 is a schematic circuit diagram of a single-ended amplifier according to the present disclosure.

The output of each of the operational amplifiers 306a and 306b is provided to the single-ended amplifier 308, which is shown in FIG. 12. In particular, the output of the amplifiers 306a and 306b is supplied to the positive and negative inputs of the amplifier 308. The amplifier 308 combines the output of the amplifiers 306a and 306b to provide a single output to the bandpass filter 310. The amplifier 308 includes a closed feedback circuit having a reference signal connected to ground including a resistor 308a which is connected in parallel with a capacitor 308b and in series with a resistor 308c. The parallel circuit provides a feedback signal to a feedback input and the series circuit provides a reference signal to a reference input of the amplifier 308.

Figure 13:
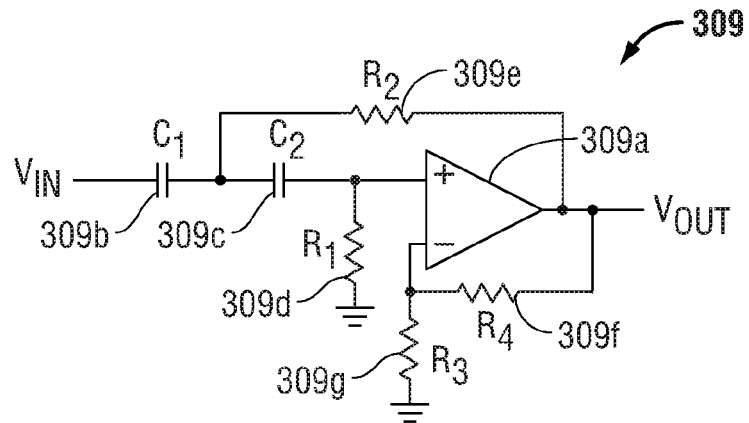
FIG. 13 is a schematic circuit diagram of a high-pass filter according to the present disclosure.
Figure 14:
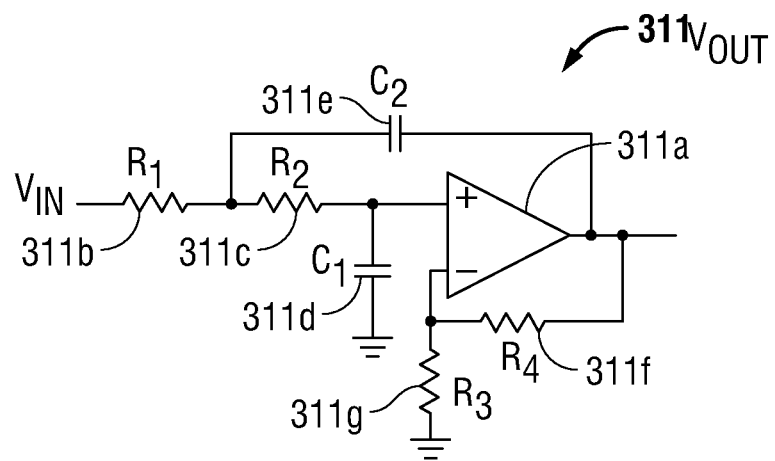
FIG. 14 is a schematic circuit diagram of a low-pass filter according to the present disclosure.
Figure 15:
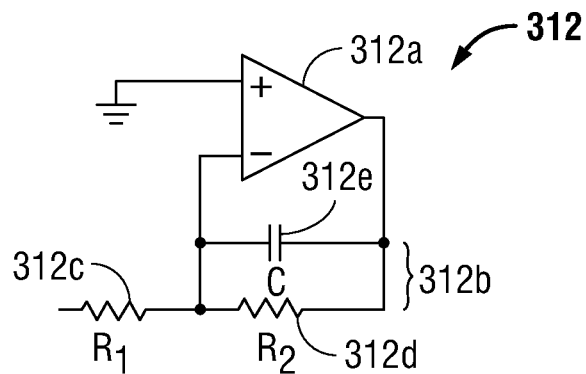
FIG. 15 is a schematic circuit diagram of an integrator according to the present disclosure.

The bandpass filter 310 includes a high-pass filter 309 and a low-pass filter 311 as shown in FIGS. 13 and 14, respectively. In embodiments, the output from the amplifier 308 may be passed through the high-pass filter 309 before being passed through the low-pass filter 311, or vice versa.

The high-pass filter 309 is configured to pass high frequencies and attenuate lower frequencies. The high-pass filter 309 includes an operational amplifier 309a. The input from the amplifier 308 or the low-pass filter 311 is provided to the positive input of the amplifier 309a having a first capacitor 309b coupled in series with a second capacitor 309c and a first resistor 309d and a second resistor 309e. The negative input of the amplifier 309a is provided by a feedback loop from a third resistor 309f coupled in series with a grounded fourth resistor 309g.

The low-pass filter 311 is configured to pass high frequencies and attenuate lower frequencies. The low-pass filter 311 includes an operational amplifier 311a. The input from the amplifier 308 or the high-pass filter 309 is provided to the positive input of the amplifier 311a having a first resistor 311b coupled in series with a second resistor 311c and a first capacitor 311d and a second capacitor 311e. The negative input of the amplifier 311a is provided by a feedback loop from a third resistor 311f coupled in series with a grounded fourth resistor 311g.

Since the voltage that is induced in the Rogowski coil 302 is proportional to the rate of change of current that is flowing through the active leads 228a the integrator 312 is utilized to provide an output voltage signal that is proportional to the current. In embodiments, a leaky integrator may be used. As used herein the term "leaky integrator" refers to an integrator having a low-pass filter as described in further detail below with respect to FIG. 14. The integrator 312 includes an amplifier 312a with a positive input thereof coupled to a ground. The input from the bandpass filter 310 is fed through a low-pass filter 312b, which includes a first resistor 312c coupled in series with a second resistor 312d that is coupled in parallel with a capacitor 312e. The second resistor 312d and the capacitor 312e are also coupled to the output of the amplifier 312a thereby providing a closed loop feedback thereto. The input signal is then fed to the negative input of the amplifier 312a. The filter 312b may be used in lieu of or in combination with the bandpass filter 310.

The integrator 312 provides a negative slope of voltage gain verses frequency. This compensates, or flattens the opposite slope of the signal coming from the coil 302. Further, the integrator 312 has extremely high DC gain. The frequency band of interest for the generator 200 is well above DC. The integrator gain may create problems if a DC offset were present at its input. The high-pass portion of the band-pass filter 310 reduces the low frequency components and reduces any DC offset, which mitigates issues caused by the integrator's amplification of these components.

Figure 16:
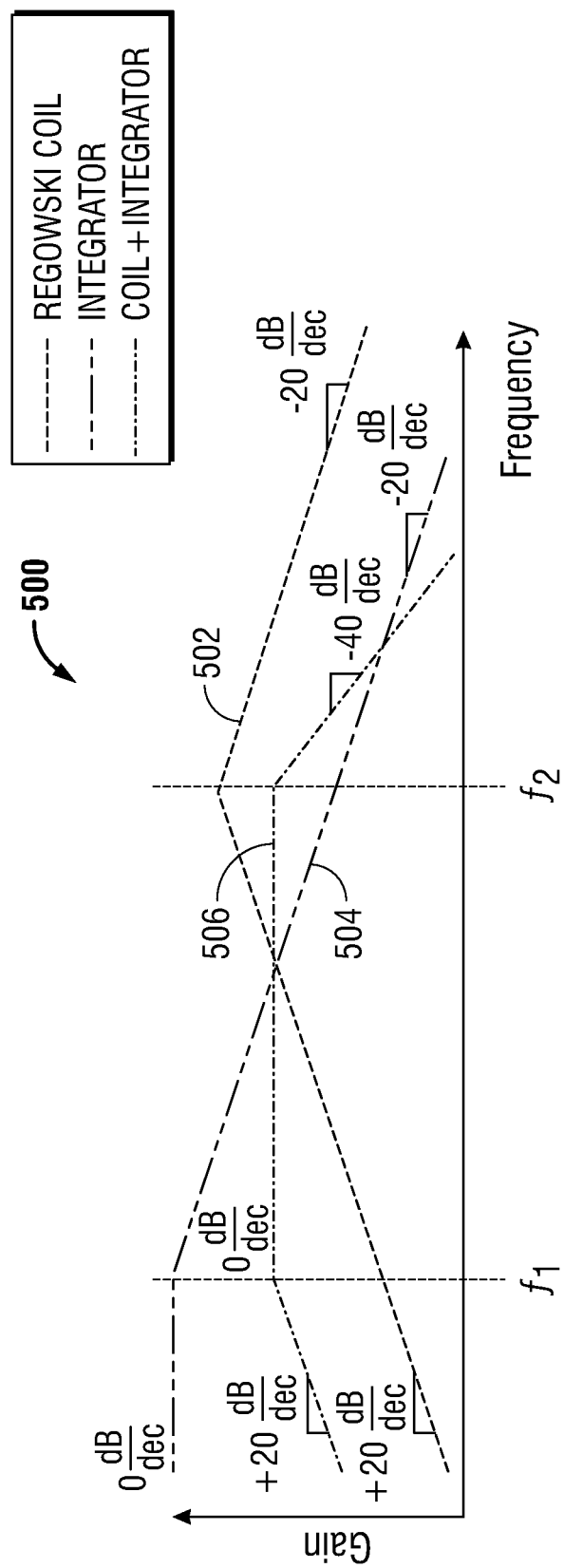
FIG. 16 is a plot of a bandwidth of the current sensor according to the present disclosure.

FIG. 16 shows a graph 500 illustrating individual gain response of the coil 302, the integrator 312, and the combined response of the coil 302 and the integrator 312. The graph 500 shows the overall response of the coil 302 as a plot 502, the response of the integrator 312 as a plot 504, and the combined response of the coil 302 and the integrator 312 of the sensor 300 as a plot 506, which is a combination of the plots 502 and 504. Frequency, f1, is determined by the response of the integrator 312 and frequency, f2, is determined by the resonant frequency of the coil 302.

Figure 17:
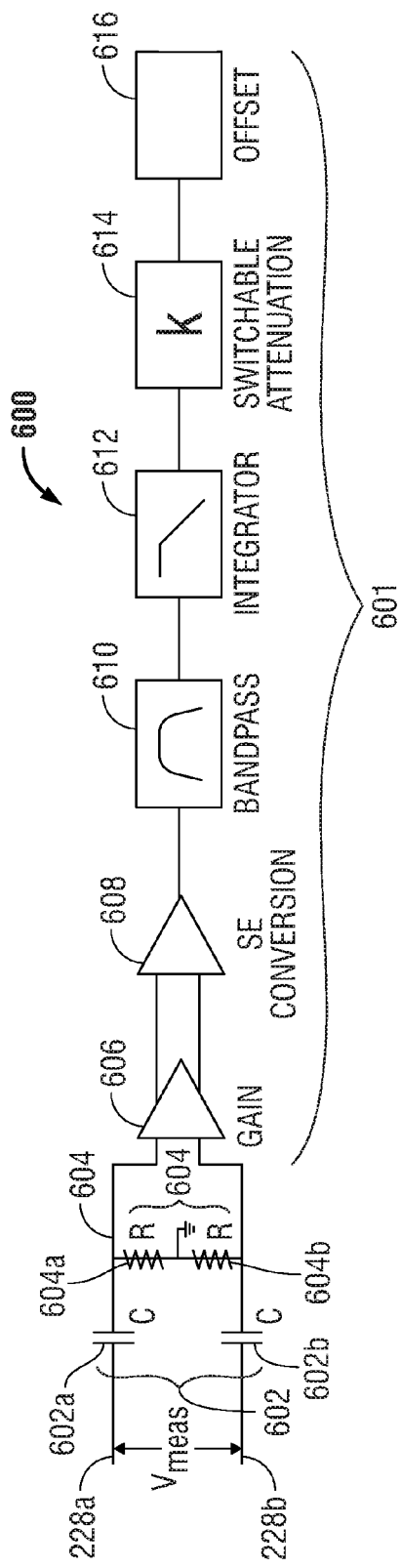
FIG. 17 is a schematic diagram of a voltage sensor according to the present disclosure.

FIG. 17 shows the RF voltage sensor 600. The sensor 600 is configured as a capacitive divider 602 including first and second capacitors 602a and 602b coupled to conditioning circuit 601. The conditioning circuit 601 of the sensor 600 is substantially similar to the conditioning circuit of the sensor 300 and includes the same components, which are designated using like numerals. The capacitive divider 602 is coupled to a resistor divider 604 including first and second resistors 604a and 604b. The voltage is then supplied to an optional gain amplifier 606 which increases the amplitude of the voltage signal. The gain amplifier 606 or the capacitive divider 602, if the gain amplifier 606 is not used, is coupled to a single-ended amplifier 608, which is, in turn, coupled to a bandpass filter 610. The single ended amplifier 608 is a differential-to-single-ended converter whose function is to convert the differential signal from the coil 602 to a single-ended signal. The amplifier 608 may have a monolithic configuration that provides improved common mode rejection.

The bandpass filter 610 removes higher and lower frequency components of the voltage signal which is then transmitted to an integrator 612. Since the voltage that is induced in the capacitive divider 602 is proportional to the rate of change of current that is flowing through the active and return leads 228a and 228b the integrator 612 is utilized to provide an output voltage signal that is proportional to the sensed RF voltage.

In embodiments, the integrator 612 may be coupled to switchable attenuation circuit 614, which may include one or more actively switched components. The attenuation circuit 614 may then be coupled to additional components such as an offset circuit 616, analog-digital converters, and the like prior to supplying the signal to the controller 224.

Figure 18:
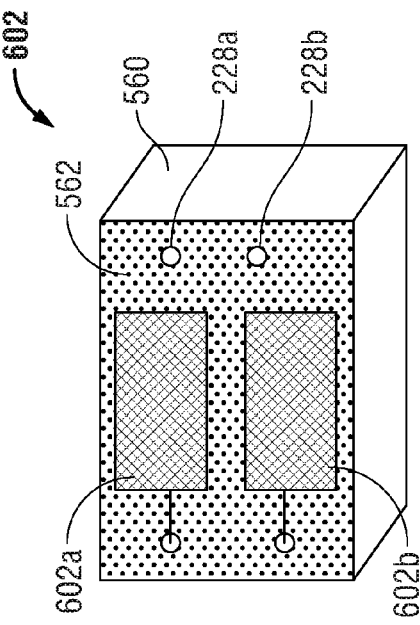
FIG. 18 is a schematic plan, cross-sectional view of the voltage sensor according to the present disclosure.

The capacitive divider 602 is shown in more detail in FIG. 18. The capacitors 602a and 602b are a matched pair of capacitors having substantially similar dielectric properties. The capacitors 602a and 602b may be plate capacitors that are disposed in a housing 560 are secured therein via a potting material 562. Potting material 562 may be any suitable dielectric material that is injection molded or otherwise provided into the housing 560. The material 562 also provides additional insulation between the capacitors 602a and 602b. The capacitive divider 602 may be disposed in proximity to the active and return leads 228a and 228b allowing the capacitors to measure the voltage therebetween.

The capacitors 602a and 602b are insulated from the active and return leads 228a and 228b and provide an isolation barrier between the patient and the generator 200. The capacitors 602a and 602b are disposed in proximity to the active and return leads 228a and 228b, such that the voltage is capacitively detected by the capacitors 602a and 602b. In other words, the capacitors 602a and 602b are capacitively coupled to the active and return leads 228a and 228b. The capacitors 602a and 602b may be plate capacitors, each having one plate connected to the active and return leads 228a and 228b and the other plate connected to the conditioning circuit 601. In embodiments, the plates of the capacitors 602a and 602b may be disposed on opposing sides of a PCB. Thus, the material (e.g., PCB) between the plates provides the insulation. As used herein the term "capacitively coupled" denotes indirect electrical contact between the capacitors 602a and 602b and the active and return leads 228a and 228b, such that electrical current passing through the return leads 228a and 228b is detected through a dielectric.

The capacitor 602a and the resistor 604a as well as the capacitor 602b and the resistor 604b combinations create similar voltage response as the coil 302. Thus, matching the gain amplifier 606, the single-ended amplifier 608, the bandpass filter 610, and the integrator 612 to the gain amplifier 306, the single-ended amplifier 308, the bandpass filter 310, and the integrator 312 allows for matching the bandpass (e.g., gain) and phase response of the sensors 300 and 600. In embodiments, the conditioning circuits 300 and 600 may have a substantially similar bandpass and phase response. As used herein, the term "substantially similar" denotes a difference between the bandpass and phase response of the conditioning circuits 300 and 600 of no more than from about 1 degree difference between voltage and current channels to about 15 degrees, in embodiments, from about 2 degrees to about 10 degrees, in further embodiments about 5 degrees. Since the integration of both current and voltage sensors 300 and 600 may be performed by identical conditioning circuit 301 and 601, the two signals are matched in gain and phase characteristics, which provides for accurate and precise representation of real power dissipated by the tissue during electrosurgery.

The capacitors 602a and 602b block the RF voltage delivered to the patient and provide a low sense voltage across the resistors 604a and 604b. The differential gain of the conditioning capacitors 602a and 602b is substantially equal to the common-mode gain due to close matching of the capacitor 602a and the resistor 604a as well as the capacitor 602b and the resistor 604b combinations. Thus, the common-mode rejection ratio effectively is the common-mode rejection ratio of the conditioning circuit 601. As a result, if the capacitors 602a and 602b and/or the resistors 604a and 604b are not matched closely, the common mode signal become a differential mode signal thereby generating an error signal.

The voltage and current sensors of the present disclosure provide various improvements over transformers in terms of isolation. In the Rogowski coil implementation the isolation and dielectric strength come from adequate wire insulation or adequate PCB material insulation. As these are inherent in the design and do not need to be applied manually as in a transformer implementation. This reduces the manufacturing costs.

Similarly, the matching of the capacitors can be accomplished via the construction techniques of the PCB manufacture. This ensures very closely matched parts. The capacitance is controlled very precisely in this instance and is much lower than in the transformer implementation. These aspects are important for patient safety and improved operation of the sensors.

Figure 19A:
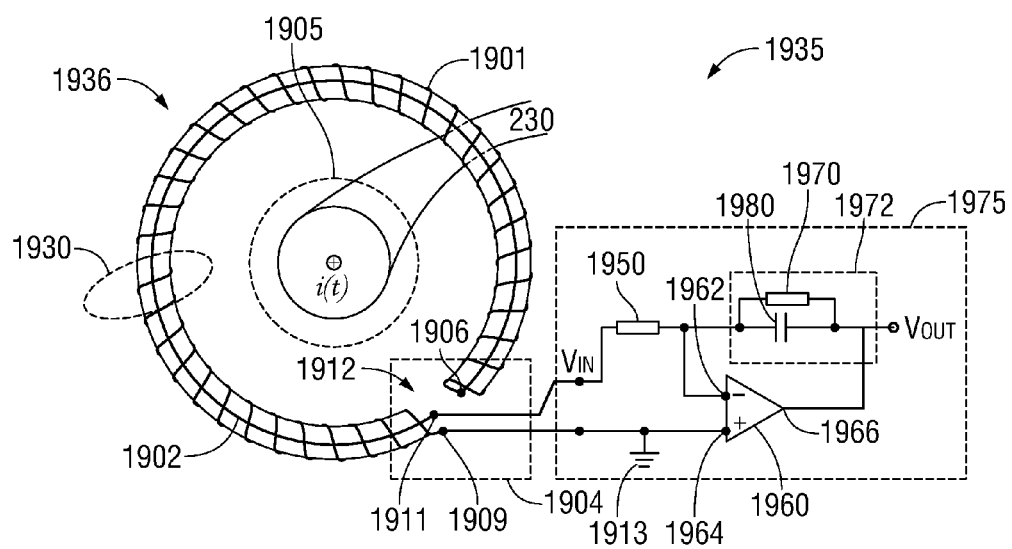
FIG. 19A is a schematic diagram of a Rogowski coil according to the present disclosure.

FIG. 19A shows a system 1935 of an embodiment of a Rogowski coil 1936 surrounding the active lead 228a that includes an AC current, current i(t), passing therethrough. The Rogowski coil 1936 includes an outer coil 1901 wrapped around an inner conductor ("bucking coil") 1902. The inner conductor 1902 and outer coil 1901 can be a single wire or conductor, or two conductors connected together at connection point 1906.

A current i(t) flowing through active lead 228a produces a first magnetic field 1905 proportional to the rate of change of the sensed current i(t). The outer coil 1901 detects the first magnetic field 1905 and produces a first voltage corresponding to the first magnetic field. The outer coil 1901 also detects a second magnetic field 1930 and produces a second voltage corresponding to the second magnetic field 1930. The second magnetic field 1930 is orthogonal to the first magnetic field 1905 and is not related to the sensed current. The inner conductor 1902 senses the second magnetic field 1930 and produces a third voltage proportional to the second magnetic field 1930. The second voltage and third voltage have approximately the same magnitude and are reduced by connecting the outer coil 1901 with the inner coil 1902 at the connection point 1906 to attain the first voltage which is indicative of the current i(t).

The Rogowski coil 1936 is connected to conditioning circuitry 1975 though connections 1909 and 1911. A first end of the outer coil 1901 connects to a first input 1964 (positive input) of operational amplifier 1960 through connection 1909. The first end of the outer coil 1901 is also connected to a ground through connection 1913. Connection 1911 connects a second end of the inner conductor 1902 (alternatively, a second end of the outer coil when a single conductor is used) to a second input 1962 (negative input) of the operational amplifier 1960 via a first resistor 1950. The first resistor may be about 1 kilo ohms (kΩ) to about 1,000 kΩ. The operational amplifier 1960 amplifies the voltage from connections 1909 and 1911 to provide an output 1966. A filter 1972 is connected in parallel to the operational amplifier 1960. The filter 1972 may be an RC filter with resistor 1970 and capacitor 1980. The resistor may be about 33 kΩ to about 3330 kΩ and the capacitor may be from about 1 nano farad (nF) to about 100 nF.

The outer coil 1901 may include an air core or a core formed from any other suitable dielectric material, which provides a low inductance within the coil. The inductance of the coil may be calculated using formula II (described above). As the load impedances are in parallel, the impedance of the coil is the dominant impedance because the coil 1936 has the lower impedance.

When active lead 228a supplies a large voltage with a small current, an undesirable fourth voltage may be produced in the Rogowski coil 1936. The fourth voltage may come from a gap 1912 in Rogowski coil 1936 which results in an undesirable magnetic field in a region 1904 and/or from discontinuities at connections 1906, 1909, and/or 1911. The fourth voltage is capacitively coupled from the active lead 228a to any conductor in the coil (e.g., connection 1911). If the coil is symmetrical then the value of coupling will be equal and thus canceled by the differential amp.

Figure 19B:
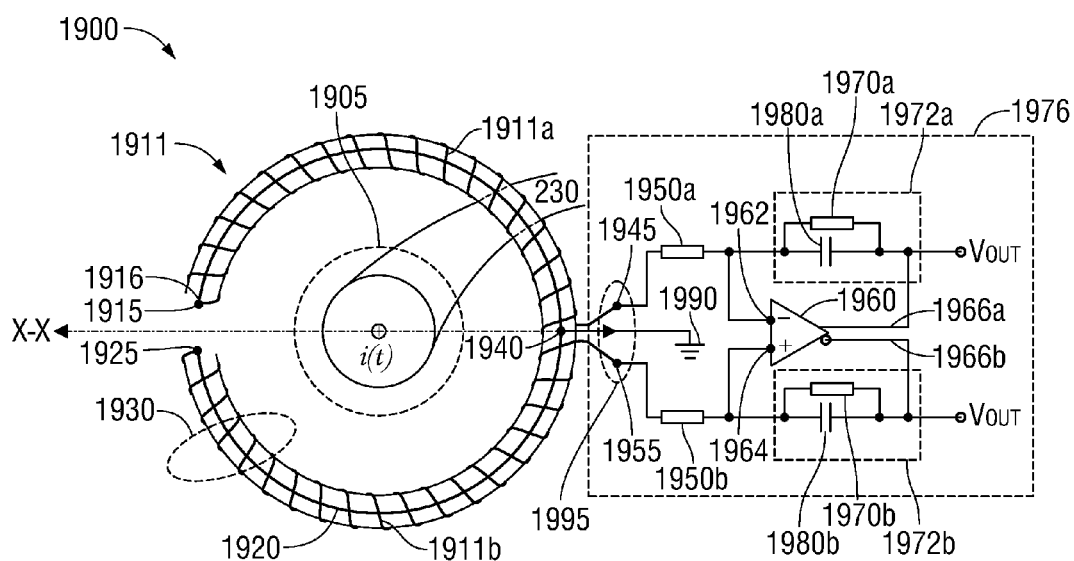
FIG. 19B is a schematic diagram of a symmetric Rogowski coil according to the present disclosure.

FIG. 19B shows a system of a symmetric Rogowski coil 1900 surrounding active lead 228a. The symmetric Rogowski coil 1900 is symmetric about axis X-X with an outer coil 1911 formed of a first portion 1911a and a second portion 1911b disposed in each side of axis X-X. The first portion 1911a of the outer coil 1911 connects to conditioning circuitry 1976 configured as a differential amplifier at a first connection 1945. The second portion 1911b of the outer coil 1911 connects to conditioning circuitry 1976 at a second connection 1955.

An inner conductor 1920, also called a "bucking" coil, runs within the outer coil 1911. The inner conductor 1920 is connected to a ground 1990 by a third connection 1940. A first end 1915 of inner conductor 1920 is connected to a second end 1916 of the first portion 1911a of the outer coil 1911, at the opposite side of the coil 1911, namely, at about 180° with respect to any of connections 1940, 1945, or 1955. The second end 1925 of inner conductor 1920 is connected to a second end 1912 of the second portion 1911b of the outer coil 1911 at the opposite side of the coil 1911 along the axis X-X, namely, at about 180° with respect to any of connections 1940, 1945, or 1955.

The current i(t) flowing through active leads 228a produces a first magnetic field 1905 proportional to the rate of change of the sensed current i(t). The outer coil 1911 detects the first magnetic field 1905 and produces a first voltage corresponding to the first magnetic field 1905. The outer coil 1911 also detects a second magnetic field 1930 and produces a second voltage corresponding to the second magnetic field 1930. The second magnetic field 1930 is orthogonal to the first magnetic field 1905 and is not related to the sensed current. The inner conductor 1920 senses the second magnetic field 1930 and produces a third voltage corresponding to the second magnetic field 1930. The second voltage and third voltage have approximately the same magnitude and are removed through conditioning circuitry 1976.

A fourth voltage occurs at the first connection 1945 due to capacitive coupling of the active lead 228a and is approximately the same because the Rogowski coil 1900 is symmetric. The fourth voltage is removed by the operational amplifier 1960 as a common mode voltage to attain the first voltage which is indicative of the current i(t).

The conditioning circuitry 1976 includes operational amplifier 1960 and two filters 1972a, 1972b. The first portion 1911a of the outer coil 1911 is connected to the negative terminal 1962 of the operational amplifier 1960 via a first resistor 1950a. The second portion 1911b of the outer coil 1911 is connected to the positive terminal 1964 of the operational amplifier 1960 via another first resistor 1950b. The first resistors 1950a or 1950b may be from about 1 kΩ to about 1,000 kΩ. The operational amplifier 1960 amplifies and integrates the voltage received from connections 1945 and 1955 and supplies differential output shown as outputs 1966a and 1966b. Filters 1972a and 1972b are connected in parallel to operational amplifier 1960. The filters 1972a and 1972b may be RC filters each including second resistors 1970a, 1970b and capacitors 1980a, 1980b in parallel, respectively. The second resistor 1970a, 1970b may be from about 33 kΩ to about 3330 kΩ and the capacitor may be from about 1 nF to about 100 nF.

Both portions 1911a and 1911b of the outer coil 1911 have an air core or any other suitable core material, which provides a low inductance within the outer coil 1910. The impedance between the positive input 1964 or negative input 1962 of the operational amplifier 1960 is equal to about two times the first resistors 1950a, 1950b and is balanced. The inductance of coil 1900 may be calculated using Formula II (described above). As the load impedances are in parallel, then impedance of the coil is the dominant impedance since the coil 1900 has the lowest impedance. Further, the impedance of the symmetric coil 1900 is about half the coil 1936.

Figure 20:
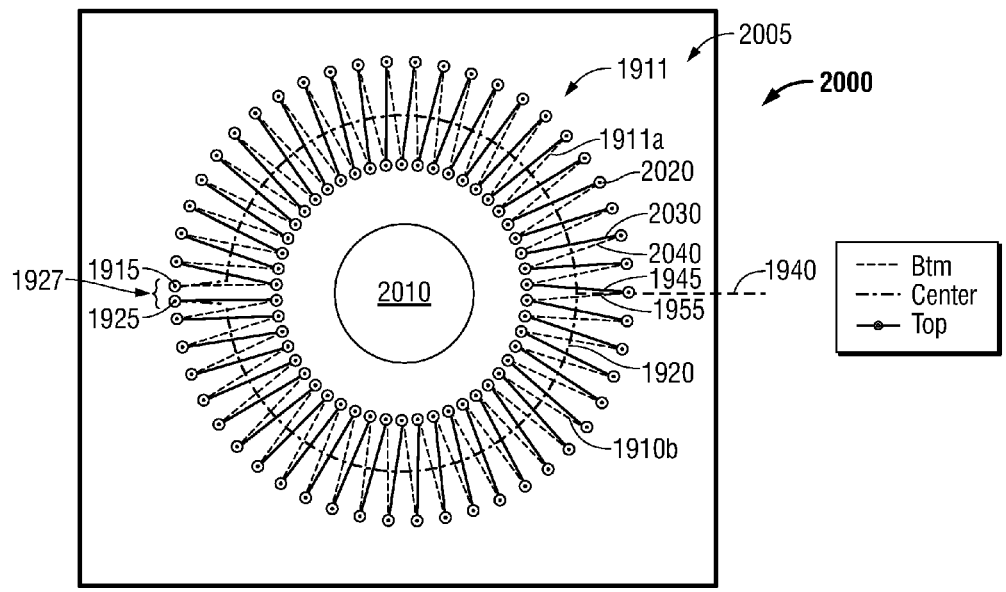
FIG. 20 is a top view of a symmetric Rogowski coil disposed on a printed circuit board according to the present disclosure.

Above described embodiment of coil 1911 of FIG. 19B may be implemented on a printed circuit board (PCB). FIG. 20 is a top view of a symmetric printed Rogowski coil 2000 disposed on a PCB 2005 with opening 2010. Opening 2010 is of sufficient size to allow active lead 228a to pass through, but also small enough to maintain active lead 228a approximately in the center for the Rogowski coil 2000. Alternatively, a symmetric fixture (not shown) may be used to attach the active lead 228a to the printed Rogowski coil 2000 and center the active lead 228a within the printed Rogowski coil 2000. In another alternative, the active lead 228a may be a rigid conductor that goes between a first circuit PCB below (not shown) and a second circuit PCB (not shown) above the printed Rogowski coil 2000 on PCB 2005 through opening 2010. The PCB 2005 and the first and second PCBs then include mounting holes and a fixture (not shown) to hold the each PCB parallel in a stack arrangement.

Similar to FIGS. 5-6, the symmetric Rogowski coil 2000 includes top lines 2030 printed on the top side of the PCB 2005 and bottom lines 2040 printed on the bottom side of the PCB 2005 connected together with vias 2020. The vias 2020 extend completely through the PCB 2005. An intentional gap 1927 is formed at a discontinuity between connections 1915 and 1925 because vias 2020 extend completely through PCB 2005, which does not allow connections 1915 and 1920 to each connect to inner conductor 1920 in the same x-y location.

Figure 21:
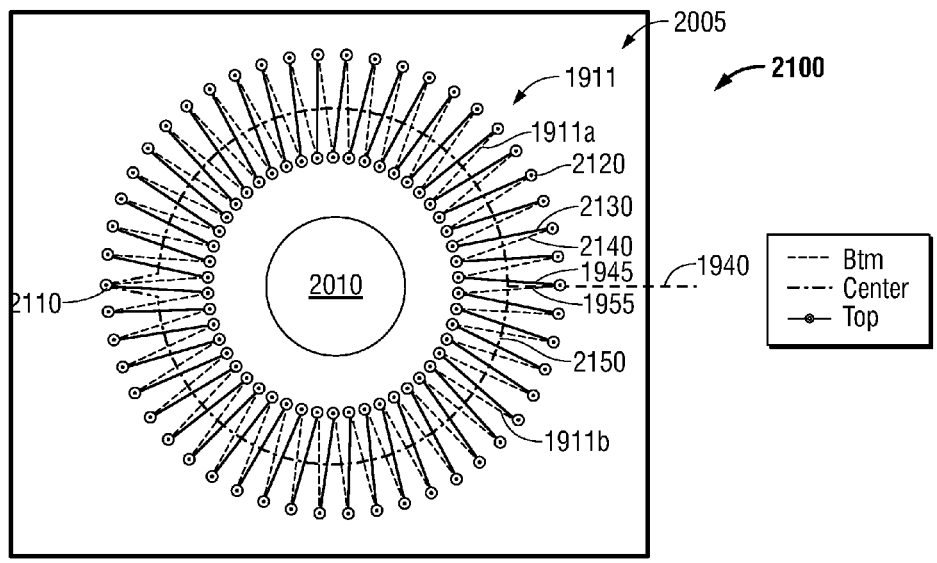
FIG. 21 is a top view of an alternative symmetric Rogowski coil disposed on a printed circuit board according to the present disclosure.

FIG. 21 is a top view of an alternative symmetric Rogowski coil 2100 disposed on PCB 2005. Vias 2120 are buried vias and connect internal layers without being exposed on either surface of the PCB 2005. The outer coil 1911 is printed on two outer layers 2130, 2140 of the PCB 2005 and connected together with buried vias 2120. The inner conductor 1920 is printed on a third layer 2150, which is between layers 2130 and 2140. Inner conductor 1920 connects separately to first portion 1911a and to the second portion 1911b of the outer coil 1911 via connection 2110. Connection 2110 is a buried via and provides for the inner conductor 1920 to connect to each portion 1911a, 1911b of the outer coil 1911 at the same x-y location.

In a printed circuit board, the gain of a Rogowski coil is limited by the number of windings or printed lines that may be used. In an alternative embodiment, a Rogowski coil may include a plurality of outer coils arranged on flex printed circuit boards (PCBs) that are folded into an accordion-type arrangement with an active lead or wire extending through the center of each of the outer coils as shown in FIGS. 22-27B. As the number of outer coils arranged in the accordion arrangement increases, the gain of the Rogowski coil increases which allows for a more accurate measurement of current of the active lead 228a.

Figure 22:
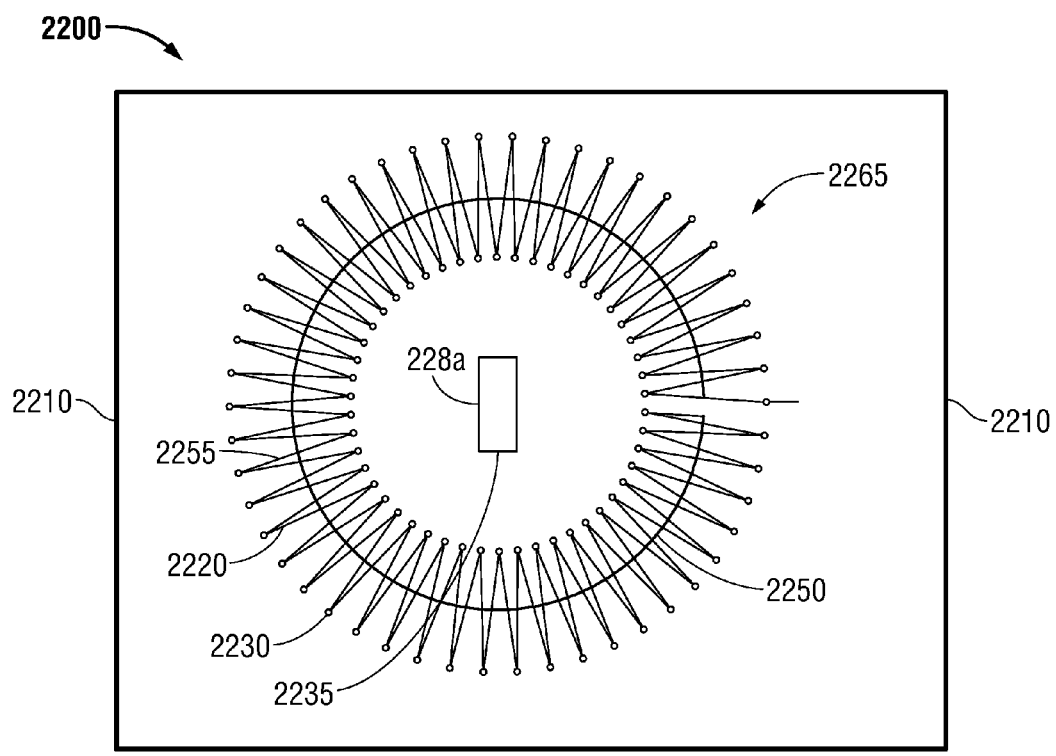
FIG. 22 is a top view of the plurality of layers of flex printed circuit boards (PCBs) according to the present disclosure.
Figure 23A:
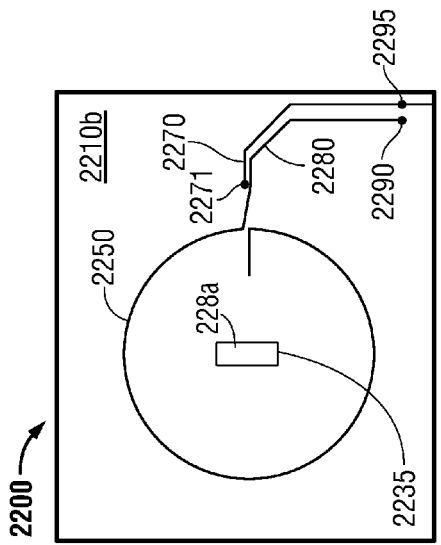
FIGS. 23A-23D are top views of a plurality of layers of flex PCBs separated apart FIG. 22.

FIG. 22 is a top view of a current sensor 2200 dispose on flexible printed circuit board (PCB) 2100 including plurality of flex PCB layers 2210a-2210d (FIGS. 23A-D) overlaid to form a Rogowski coil 2265. The flexible PCB 2100 may be formed from any suitable flexible dielectric material. FIGS. 23A-23D are top views of each of the plurality of flex PCB layers 2210a-2210d of the current sensor 2200 shown in FIG. 22. FIG. 23A shows a first flex PCB layer 2210a of the plurality including a plurality of top conductive traces 2220 that extend between vias 2230 and form an upper portion 2267a of an outer coil 2267 of Rogowski coil 2265. The vias 2230 extend through the first flex PCB layer 2210. The first layer 2210 also includes opening 2235 in which active lead 228a passes through. With reference to FIG. 23C, a third flex PCB layer 2210c of flex PCB includes a plurality of bottom conductive traces 2255 that extend between vias 2230 to form a bottom portion 2267b of the outer coil 2267 of the Rogowski coil 2265.

Figure 23B:
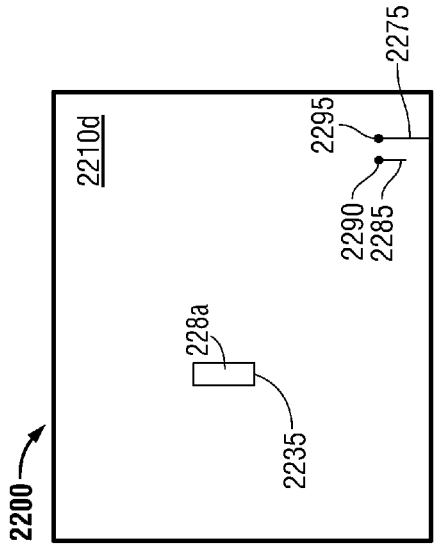
Figure 23C:
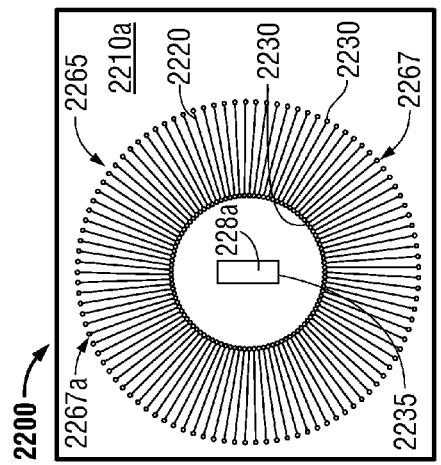
Figure 23D:
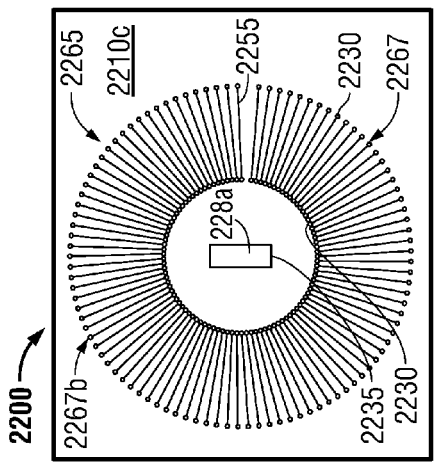
Figure 24A:
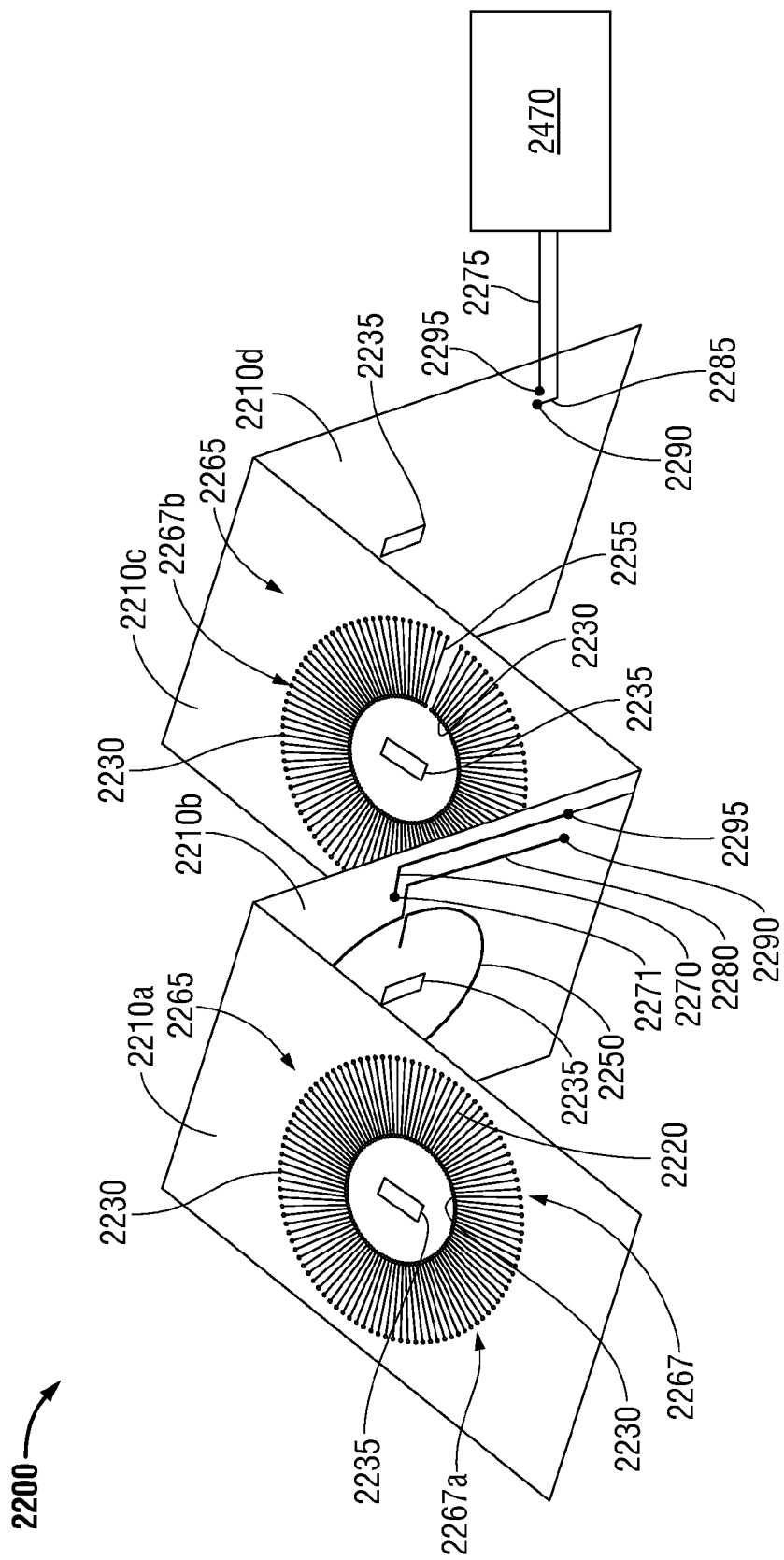
FIG. 24A is a perspective view of a Rogowski coil system according to the present disclosure.

FIG. 23B shows a second flex PCB layer 2210b of the plurality of flex PCBs 2200, and includes an inner conductor ("Bucking Coil") 2250. Lead 2280 connects inner conductor 2250 to a via connection 2290. Lead 2270 connects to a top conductive trace of the plurality of top conductive traces 2220 and/or a bottom conductive trace of the plurality of bottom conductive traces 2255 of the lower portion 2267b of the outer coil 2267 through a via connection 2271. The top conductive traces 2220 and bottom conductive traces 2255 form the outer coil 2267 around active lead 228a with the inner conductor 2250 disposed within the outer coil 2267. Connection 2295 connects lead 2270 and lead 2275 together. Lead 2275 then connects the Rogowski coil 2265 to conditioning circuitry 2470 (FIG. 24A). The conditioning circuitry may be any suitable circuitry for differentiating the voltage signal of the Rogowski coil 2265 described above. With reference to FIG. 23D, a fourth flex PCB layer 2210d of flex PCB 2200 includes connection 2290 that connects lead 2280 of the second flex PCB layer 2210b to lead 2285 of the fourth flex PCB layer 2210d, which then connects the inner conductor 2250 to conditioning circuitry 2470.

Figure 24B:
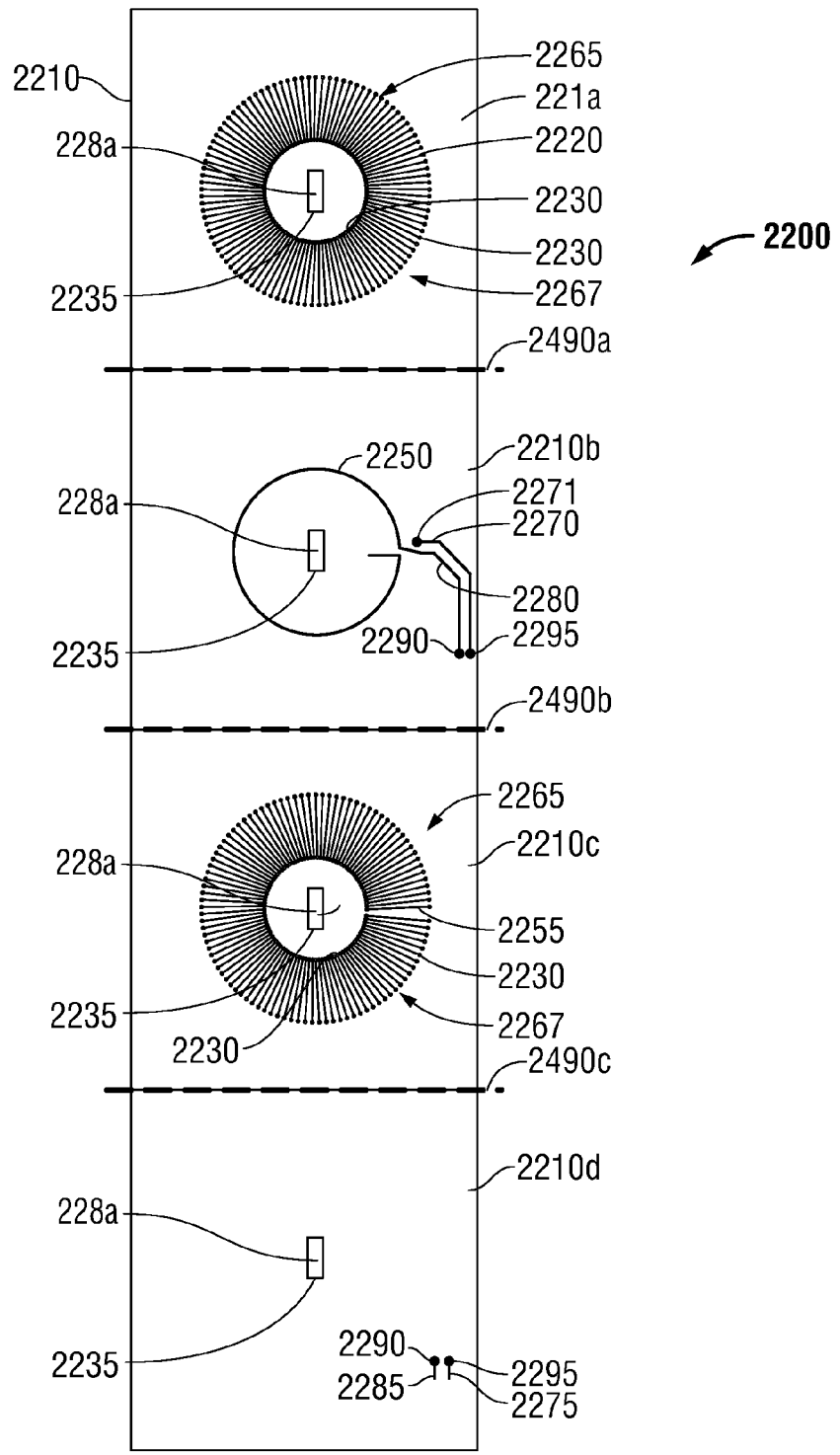
FIG. 24B is a top view of the Rogowski coil shown in FIG. 24B.

With reference to FIGS. 24A-24B, the current sensor 2200 is shown in partially folded and unfolded configuration, respectively. FIG. 24A is a perspective view of the current sensor 2220 including the accordion style Rogowski coil 2265 and conditioning circuitry 2470 in a partially folded configuration. FIG. 24B is a top view of the plurality of flex PCB layers 2210a-2210d in an unfolded configuration. Flex PCB 2411 may include fold lines 2490a, 2490b, 2490c in forming the accordion Rogowski coil 2265. Each of the flex PCB layers 2210a-d includes a plurality of printed conductive traces and vias as described above with respect to FIGS. 23A-23D. As the PCB layers 2210a-2210d are folded over about the fold lines 2490a-2490c e.g., layering each of the flex PCB layers 2210a-2210d to form the current sensor 2200, such that the connections are formed therebetween thereby forming the current sensor 220.

The current i(t) flowing through active lead 228a produces a first magnetic field proportional to the rate of change of the sensed current i(t). The outer coil 2265 detects the first magnetic field and produces a first voltage corresponding to the first magnetic field. The outer coil 2265 also detects a second magnetic field and produces a second voltage corresponding to the second magnetic field. The second magnetic field is orthogonal to the first magnetic field and is not related to the sensed current. The inner conductor 2250 senses the second magnetic field and produces a third voltage proportional to the second magnetic field. The second voltage and third voltage have approximately the same magnitude and are reduced by connecting the outer coil 2266 with the inner coil 2250 to attain the first voltage which is indicative of the current i(t).

Figure 25:
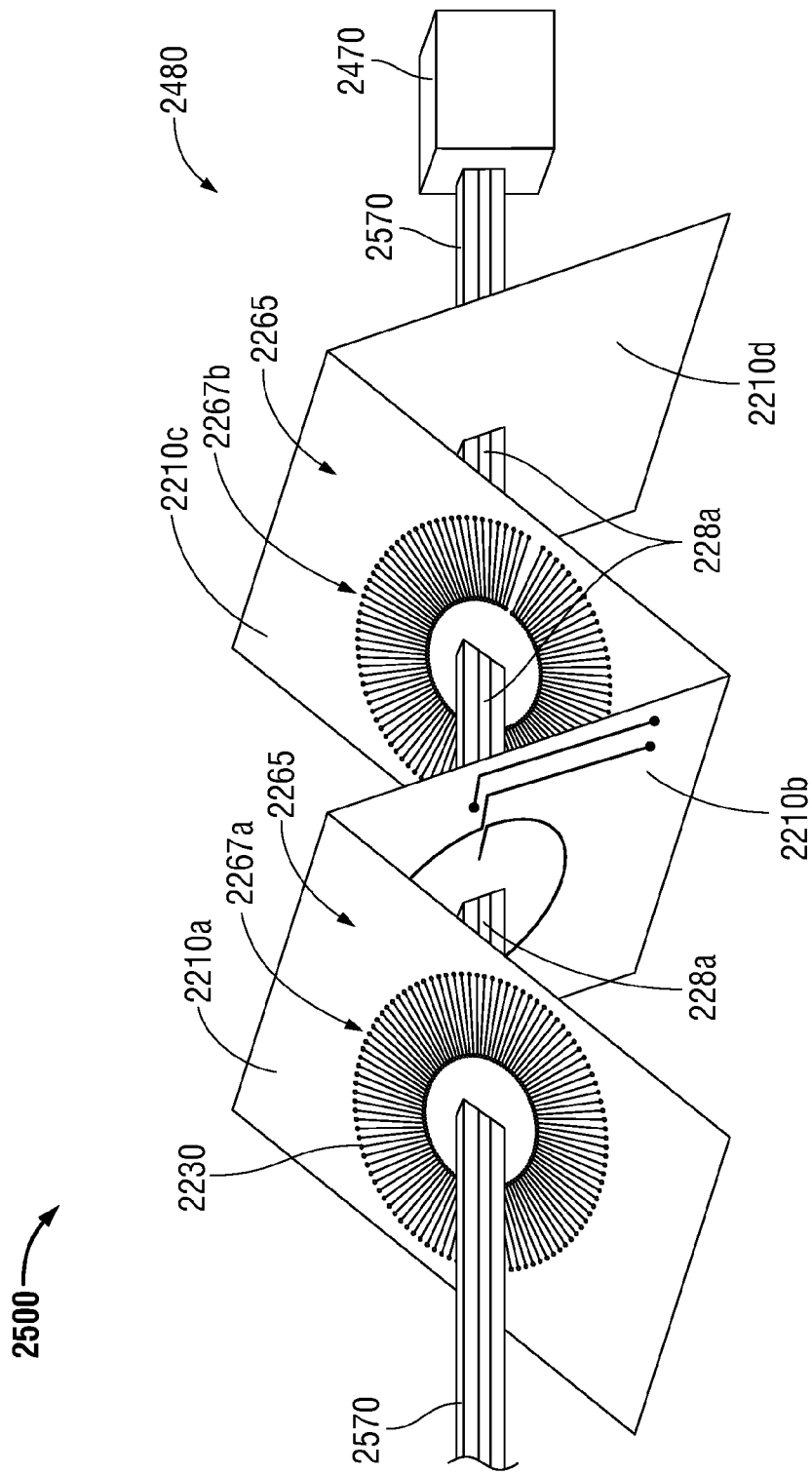
FIG. 25 a perspective view of a Rogowski coil system according to the present disclosure.

FIG. 25 shows another embodiment of the current sensor 2200 disposed over a circuit board 2570 having the active lead 228a and the conditioning circuit 2470. The current sensor 220 includes the Rogowski coil 2265 disposed in an accordion configuration about the circuit board 2570.

Figure 26:
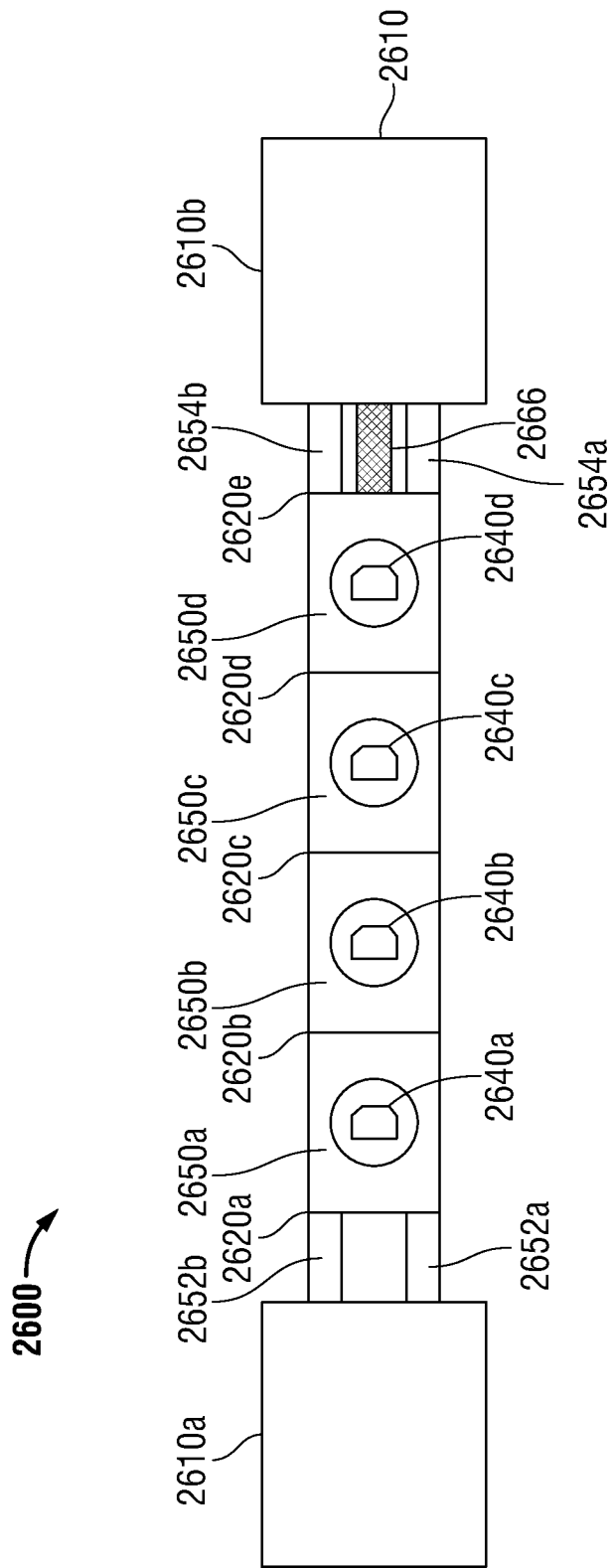
FIG. 26 is a top view of a flex circuit Rogowski coil system according to the present disclosure.

FIG. 26 shows a further embodiment of the current sensor 2600, which is substantially similar to the current sensor 2200 having a Rogowski coil (not shown) disposed on a flexible PCB 2650 having a plurality of layers 2650a-2650d, each having a self-aligning feedhole 2640a-2640d, respectively, therethrough. The flexible PCB 2650 is coupled to a circuit 2610. The circuit 2610 may be disposed on a rigid PCB. The circuit 2610 may include conditioning circuitry for processing the signal from the current sensor 2600. The flexible PCB 2650 interconnects two portions 2610a, 2610b of the circuit 2610. In particular, the flexible PCB 2650 includes a pair of flaps 2652a, 2652b coupled to the first portion 2610a and a pair of flaps 2654a, 2654b coupled to the second portion 2610b. The flaps 2652a, 2652b and 2654a, 2654b are separated by a gap allowing for a contact 2666 (e.g., active lead 228a) to be disposed therebetween. The flaps 2652a, 2652b, layers 2650a-2650d, and flaps 2654a, 2654b are separated by fold lines 2620a-2620e, respectively. This allows the flexible PCB 2650 to be folded as the two portions 2610a, 2610b of the circuit 2610 are brought together with the contact 2666 (e.g., active lead 228a) to couple the portions 2610a, 2610b.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A current sensor comprising:
   a printed circuit board including an upper layer, a lower layer, and an intermediate layer coupled to the upper and lower layers, each of the upper layer, the lower layer, and the intermediate layer has an opening defined therethrough, the printed circuit board being movable between a first configuration and a second configuration,
   in the first configuration, the upper portion, the lower portion, and the inner conductor are disposed in the same plane,
   in the second configuration, at least one of the upper portion, the lower portion, or the inner conductor is disposed at an angle relative to another of the upper portion, the lower portion, or the inner conductor and the opening of each of the upper layer, the lower layer, and the intermediate layer is coaxial with one another such that at least one lead is disposable through the opening of each of the upper layer, the lower layer, and the intermediate layer; and
   a sensor assembly including:
      an outer coil having:
         an upper portion disposed on the upper layer of the printed circuit board; and
         a lower portion disposed on the lower layer of the printed circuit board; and
      an inner conductor disposed on the intermediate layer of the printed circuit board.

2. The current sensor according to claim 1, wherein the upper portion and the lower portion of the outer coil are interconnected by a plurality of vias.

3. The current sensor according to claim 1, wherein the upper layer, the lower layer, and the intermediate layer are folded over each other to enclose the inner conductor between the upper and lower portions of the outer coil.

4. The current sensor according to claim 1, wherein the outer coil and the inner conductor are coupled to a conditioning circuit.

5. The current sensor according to claim 4, wherein the sensor assembly is configured to output a differentiated signal corresponding to a current passing through the at least one lead.

6. The current sensor according to claim 5, wherein the conditioning circuit is configured to integrate the differentiated signal to output a processed current signal indicative of the current.

7. The current sensor according to claim 5, wherein the conditioning circuit includes a first portion and a second portion interconnected by the printed circuit board.

8. The current sensor according to claim 7, wherein the at least one lead is disposed between the first and second portions of the conditioning circuit.

9. The current sensor according to claim 4, wherein the printed circuit board includes a fourth layer pivotably coupled to the lower layer, the fourth layer connecting the inner conductor to the conditioning circuit.

10. The current sensor according to claim 1, wherein printed circuit board is flexible.

* * * * *